United States Patent
Echigo et al.

(10) Patent No.: US 9,920,024 B2
(45) Date of Patent: Mar. 20, 2018

(54) METHOD FOR PURIFYING COMPOUND OR RESIN

(71) Applicant: Mitsubishi Gas Chemical Company, Inc., Tokyo (JP)

(72) Inventors: Masatoshi Echigo, Kanagawa (JP); Takashi Makinoshima, Kanagawa (JP); Naoya Uchiyama, Kanagawa (JP)

(73) Assignee: Mitsubishi Gas Chemical Company, Inc., Tokyo (JP)

(*) Notice: Subject to any disclaimer, the term of this patent is extended or adjusted under 35 U.S.C. 154(b) by 0 days.

(21) Appl. No.: 15/100,009

(22) PCT Filed: Nov. 28, 2014

(86) PCT No.: PCT/JP2014/081508
§ 371 (c)(1),
(2) Date: May 27, 2016

(87) PCT Pub. No.: WO2015/080240
PCT Pub. Date: Jun. 4, 2015

(65) Prior Publication Data
US 2017/0001972 A1  Jan. 5, 2017

(30) Foreign Application Priority Data
Nov. 29, 2013 (JP) ................................. 2013-248012

(51) Int. Cl.
*C07D 311/94* (2006.01)
*C07D 311/92* (2006.01)

(52) U.S. Cl.
CPC ................................ *C07D 311/92* (2013.01)

(58) Field of Classification Search
CPC ........................... C07D 311/92; C07D 311/96
USPC ......................................................... 549/382
See application file for complete search history.

(56) References Cited

U.S. PATENT DOCUMENTS

| | | | | |
|---|---|---|---|---|
| 5,073,622 A | * | 12/1991 | Wojtech | C08G 8/10 528/129 |
| 2012/0220112 A1 | | 8/2012 | Hatakeyama et al. | |
| 2012/0271020 A1 | | 10/2012 | Suzuki | |
| 2014/0248561 A1 | | 9/2014 | Echigo et al. | |
| 2015/0090691 A1 | * | 4/2015 | Echigo | C07D 311/96 216/49 |

FOREIGN PATENT DOCUMENTS

| | | |
|---|---|---|
| EP | 0754975 A2 | 1/1997 |
| EP | 2743770 A1 | 6/2014 |
| JP | H05-019463 A | 1/1993 |
| JP | 3052449 B2 | 6/2000 |
| JP | 2002-182402 A | 6/2002 |
| JP | 2012-190000 A | 10/2012 |
| JP | 2012-224793 A | 11/2012 |
| WO | 2013-024778 A1 | 2/2013 |
| WO | 2013-024779 A1 | 2/2013 |

OTHER PUBLICATIONS

Echigo et al. "Development of new xanthendiol derivatives applied to the negative-tone molecular resists for EB/EUVL," vol. 8682, Mar. 29, 2013, p. 86821V (8 pages).
International Search Report dated Mar. 3, 2014 for PCT/JP2014/081508 and English translation of the same (6 pages).

* cited by examiner

*Primary Examiner* — T. Victor Oh
(74) *Attorney, Agent, or Firm* — Fitch, Even, Tabin & Flannery LLP

(57) ABSTRACT

The method according to the present invention is a method for purifying a compound represented by a specific formula (1) or a resin having a structure represented by a specific formula (2), the method including a step of bringing a solution (A) including an organic solvent optionally immiscible with water, and the compound or the resin into contact with an acidic aqueous solution.

13 Claims, No Drawings

METHOD FOR PURIFYING COMPOUND OR RESIN

CROSS-REFERENCE TO RELATED APPLICATIONS

This application is a U.S. national phase application filed under 35 U.S.C. § 371 of International Application PCT/JP2014/081508, filed on Nov. 28, 2014, designating the United States, which claims priority from Japanese Application Number 2013-248012, filed Nov. 29, 2013, which are hereby incorporated herein by reference in their entirety.

Field of the Invention

The present invention relates to a method for purifying a compound or a resin having a specific structure.

Background of the Invention

A compound or a resin having a benzoxanthene backbone is excellent in heat resistance, etching resistance and solvent solubility, and therefore is used for semiconductor coating agents, resist materials and semiconductor underlayer film formation materials (see, for example, Patent Documents 1 to 2).

CITATION LIST

Patent Document

Patent Document 1: International Publication No. WO2013/024778
Patent Document 2: International Publication No. WO2013/024779

SUMMARY

In the above applications, in particular, the metal content is an important performance item for an enhancement in yield. That is, when a compound or a resin having a benzoxanthene backbone, high in the metal content, is used, the metal remains in a semiconductor to result in a reduction in electrical properties of the semiconductor, and therefore a reduction in the metal content is demanded.

As a method for producing a compound or a resin having a benzoxanthene backbone, having a reduced metal content, for example, there are considered a method of bringing a mixture including the compound or the resin and an organic solvent into contact with an ion-exchange resin, and a method of filtering the mixture by a filter.

If various metal ions are contained, however, the method using an ion-exchange resin has the problem of having difficulty in selection of the ion-exchange resin and thus having difficulty in removal of the metal ions depending on the kinds of the metals, the problem of having difficulty in removal of a nonionic metal, and also the problem of being large in running cost.

On the other hand, the method of filtering by a filter has the problem of having difficulty in removal of an ionic metal. Accordingly, it is demanded to establish an industrially advantageous purification method of a cyclic compound having a reduced metal content.

The present invention has been made in view of the above problems of the prior art, and an object of the present invention is to provide a purification method that enables to reduce the contents of various metals that can be included as impurities in a specific compound or resin having a specific structure.

The present inventors have intensively studied in order to solve the above problems, and as a result, have found that a solution including a compound or a resin having a specific structure and a specific organic solvent is brought into contact with an acidic aqueous solution to result in a reduction in the contents of various metals, thereby leading to the present invention.

That is, the present invention is as follows.

[1]

A method for purifying a compound represented by the following formula (1) or a resin having a structure represented by the following formula (2), the method comprising:

a step of bringing a solution (A) comprising an organic solvent optionally immiscible with water, and the compound or the resin into contact with an acidic aqueous solution.

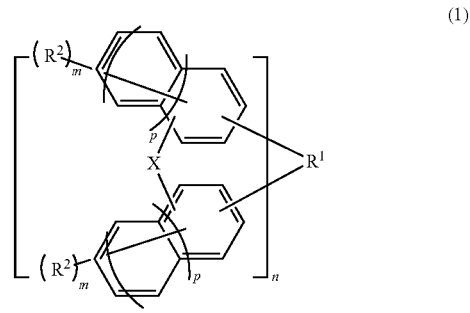

(wherein, each X independently represents an oxygen atom or a sulfur atom, $R^1$ represents a single bond or a 2n-valent hydrocarbon group having 1 to 30 carbon atoms, the hydrocarbon group optionally has a cyclic hydrocarbon group, a double bond, a hetero atom, or an aromatic group having 6 to 30 carbon atoms, and each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group, each m is independently an integer of 1 to 6, each p is independently 0 or 1, and n is an integer of 1 to 4.)

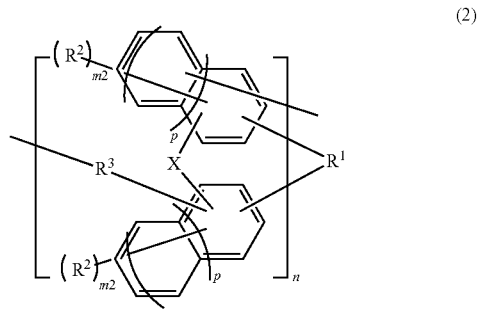

(wherein, each X independently represents an oxygen atom or a sulfur atom, $R^1$ represents a single bond or a 2n-valent hydrocarbon group having 1 to 30 carbon atoms, the hydrocarbon group optionally has a cyclic hydrocarbon group, a double bond, a hetero atom, or an aromatic group having 6 to 30 carbon atoms, each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group, each $R^3$ independently represents a single bond, or a linear or branched alkylene group having 1 to 20 carbon atoms, each $m^2$ is independently an integer of 1 to 5, each p is independently 0 or 1, and n is an integer of 1 to 4.)

[2]
The method according to [1], wherein the acidic aqueous solution is one or more aqueous solution of mineral acid selected from the group consisting of hydrochloric acid, sulfuric acid, nitric acid and phosphoric acid, or one or more aqueous solution of organic acid selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid and trifluoroacetic acid.

[3]
The method according to [1] or [2], wherein the organic solvent optionally immiscible with water is toluene, 2-heptanone, cyclohexanone, cyclopentanone, methyl isobutyl ketone, propylene glycol monomethyl ether acetate or ethyl acetate.

[4]
The method according to [1] or [2], wherein the organic solvent optionally immiscible with water is methyl isobutyl ketone or ethyl acetate.

[5]
The method according to any of [1] to [4], wherein the solution (A) comprises the organic solvent optionally miscible with water in an amount of 0.1 to 100 times by mass based on an amount of the compound represented by the formula (1) or the resin having the structure represented by the formula (2).

[6]
The method according to [5], wherein the organic solvent optionally miscible with water is N-methylpyrrolidone or propylene glycol monomethyl ether.

[7]
The method according to any of [1] to [6], further comprising a step of performing an extraction treatment with water after an extraction treatment by the step of bringing the solution (A) into contact with the acidic aqueous solution is performed.

[8]
The method according to any of [1] to [7], wherein the compound represented by the formula (1) is a compound represented by the following formula (1-1).

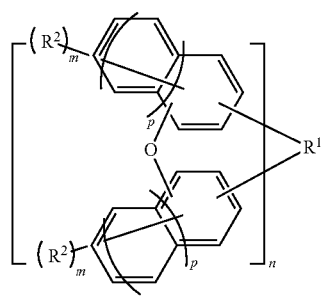
(1-1)

(wherein, $R^1$, $R^2$, m, p and n are the same as defined in the formula (1).)

[9]
The method according to [8], wherein the compound represented by the formula (1-1) is a compound represented by the following formula (1-2).

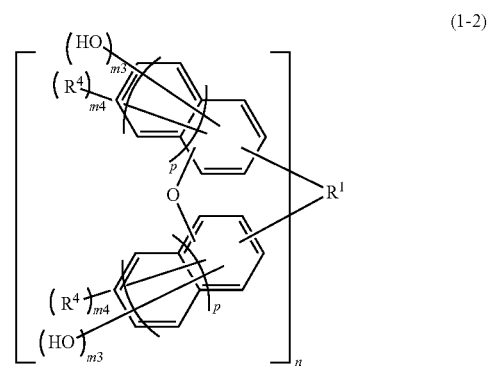
(1-2)

(wherein, $R^1$, p and n are the same as defined in the formula (1), $R^4$ is the same as $R^2$ defined in the formula (1), each $m^3$ is independently an integer of 1 to 6, each $m^4$ is independently an integer of 0 to 5, and $m^3+m^4$ is an integer of 1 to 6.)

[10]
The method according to [9], wherein the compound represented by the formula (1-2) is compound represented by the following formula (1-3).

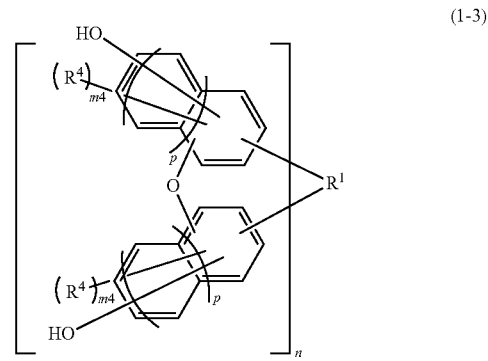
(1-3)

(wherein, $R^1$, p and n are the same as defined in the formula (1), and $R^4$ and $m^4$ are the same as defined in the formula (1-2).)

[11]
The method according to any of [1] to [7], wherein the compound represented by the formula (1) is a compound represented by the following formula (1-4).

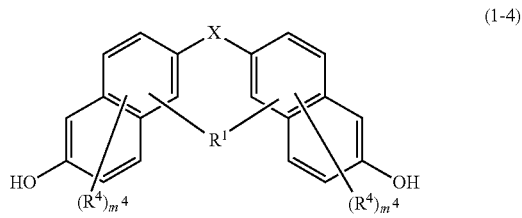
(1-4)

(wherein, X and $R^1$ are the same as defined in the formula (1), and $R^4$ and $m^4$ are the same as defined in the formula (1-2).)

[12]

The method according to [11], wherein the compound represented by the formula (1-4) is a compound represented by the following formula (1-5).

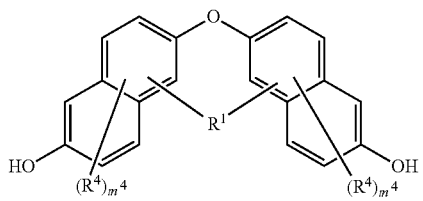

(1-5)

(wherein, $R^1$ is the same as defined in the formula (1), and $R^4$ and $m^4$ are the same as defined in the formula (1-2).)

[13]

The method according to [12], wherein the compound represented by the formula (1-5) is a compound represented by the following formula (BisN-1).

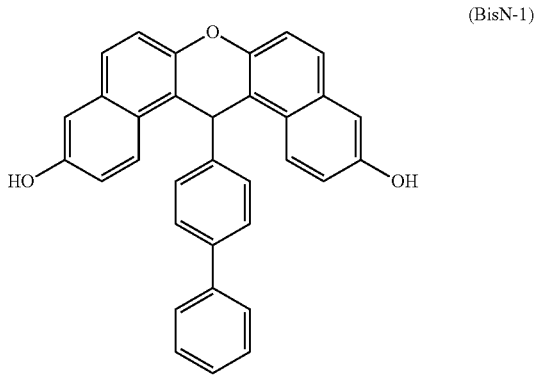 [SMILES: Oc1ccc2c3c(ccc2c1)Oc1ccc2cc(O)ccc2c1C3c1ccc(-c2ccccc2)cc1]

(BisN-1)

According to the purification method of the present invention, the contents of various metals that can be included as impurities in a compound or a resin having a specific structure can be reduced.

DESCRIPTION OF EMBODIMENTS

Hereinafter, an embodiment of the present invention will be described (hereinafter, referred to as "present embodiment"). Herein, the present embodiment is illustrative for explaining the present invention, and the present invention is not limited only to the present embodiment.

The purification method according to the present embodiment is a method for purifying a compound represented by the following formula (1) or a resin having a structure represented by the following formula (2). Furthermore, the purification method of the present embodiment includes a step of bringing a solution (A) including an organic solvent optionally immiscible with water, and the compound or the resin into contact with an acidic aqueous solution. The purification method of the present embodiment is configured as described above, and therefore enables to reduce the contents of various metals that can be included as impurities in the compound or the resin having a specific structure.

More specifically, in the present embodiment, the compound or the resin can be dissolved in the organic solvent optionally immiscible with water and furthermore the solution can be brought into contact with the acidic aqueous solution to thereby perform an extraction treatment. Thus, the metal component, which is included in the solution (A) including the compound represented by the formula (1) or the resin having a structure represented by the formula (2) and the organic solvent, can be transferred to the aqueous phase. Then, the organic phase and the aqueous phase can be separated to purify the compound represented by the formula (1) or the resin having a structure represented by the formula (2), either of which has a reduced metal content.

The compound for use in the present embodiment is a compound represented by the following formula (1).

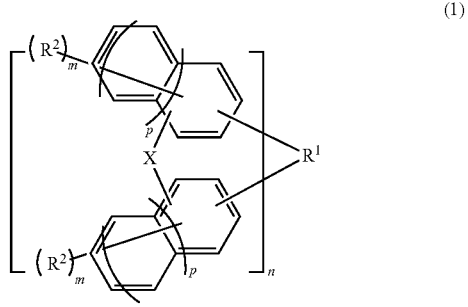

(1)

In the formula (1), each X independently represents an oxygen atom or a sulfur atom, and respective naphthalene rings are bonded with each other via X. $R^1$ represents a single bond or a 2n-valent hydrocarbon group having 1 to 30 carbon atoms, and respective naphthalene rings are bonded with each other via $R^1$. Herein, the 2n-valent hydrocarbon group optionally has a cyclic hydrocarbon group, a double bond, a hetero atom, or an aromatic group having 6 to 30 carbon atoms. Each $R^2$ independently represents a monovalent substituent selected from the group consisting of a linear, branched or cyclic alkyl group having 1 to 10 carbon atoms, an aryl group having 6 to 10 carbon atoms, an alkenyl group having 2 to 10 carbon atoms, and a hydroxyl group, and m number of $R^2$(s) is bonded to each naphthalene ring. Herein, at least one $R^2$ represents a hydroxyl group. In addition, each m is independently an integer of 1 to 6, each p is independently 0 or 1, and n is an integer of 1 to 4.

Herein, the 2n-valent hydrocarbon group means an alkylene group having 1 to 30 carbon atoms when n=1, an alkanetetrayl group having 1 to 30 carbon atoms when n=2, an alkanehexayl group having 2 to 30 carbon atoms when n=3, and an alkaneoctayl group having 3 to 30 carbon atoms when n=4. Examples of the 2n-valent hydrocarbon group include those having a linear, branched or cyclic structure.

In addition, the 2n-valent hydrocarbon group optionally has a cyclic hydrocarbon group, a double bond, a hetero atom, or an aromatic group having 6 to 30 carbon atoms. Herein, the cyclic hydrocarbon group also includes a bridged cyclic hydrocarbon group.

Here, the compound represented by the formula (1) is preferably a compound represented by the following formula (1-1) in terms of availability of raw materials.

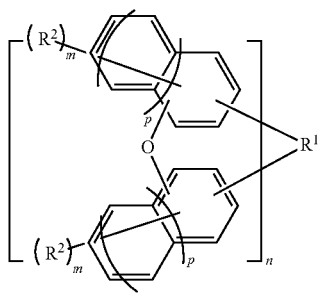

(1-1)

In the formula (1-1), $R^1$, $R^2$, m, and n are the same as defined in the formula (1).

The compound represented by the general formula (1-1) is more preferably a compound represented by the following formula (1-2) in terms of solubility in the organic solvent.

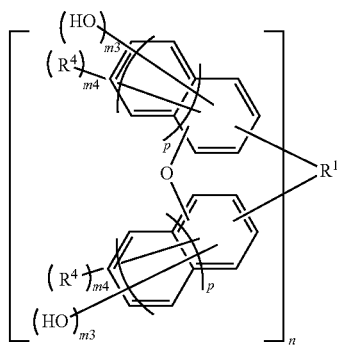

(1-2)

In the formula (1-2), $R^1$ and n are the same as defined in the formula (1), $R^4$ is the same as $R^2$ defined in the formula (1), each $m_3$ is independently an integer of 1 to 6, each $m_4$ is independently an integer of 0 to 5, and $m_3+m_4$ is an integer of 1 to 6.

The compound represented by the general formula (1-2) is further preferably a compound represented by the following formula (1-3) in terms of solubility in the organic solvent.

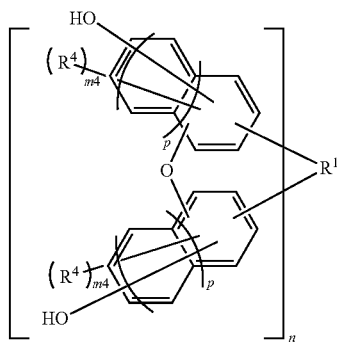

(1-3)

In the formula (1-3), $R^1$ is the same as defined in the formula (1), and $R^4$ and $m^4$ are the same as defined in the formula (1-2).

In addition, the compound represented by the formula (1) is preferably an embodiment where n=1 in the formula (1), namely, a compound represented by the following formula (1-4), in terms of having a low molecular weight.

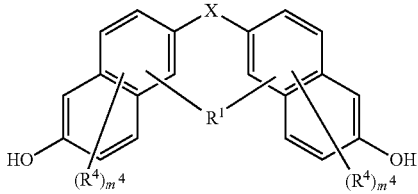

(1-4)

In the formula (1-4), X and $R^1$ are the same as defined in the formula (1), $R^4$ and $m^4$ are the same as defined in the formula (1-2).

Furthermore, the compound represented by the general formula (1-4) is more preferably an embodiment where X=O (oxygen atom) in the formula (1-4), namely, a compound represented by the following formula (1-5).

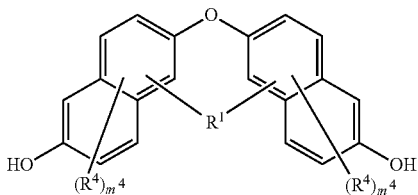

(1-5)

In the formula (1-5), $R^1$ is the same as defined in the formula (1), $R^4$ and $m^4$ are the same as defined in the formula (1-2).

Specific examples of the compound represented by the general formula (1) are shown below, but are not limited to those exemplified herein.

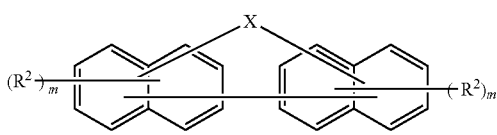

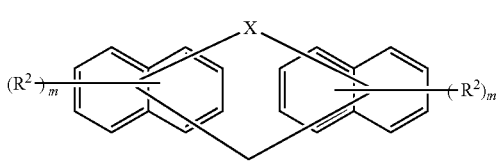

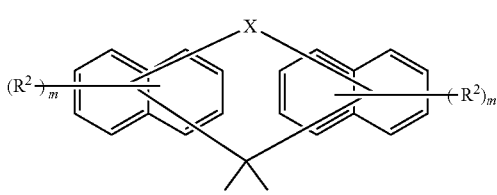

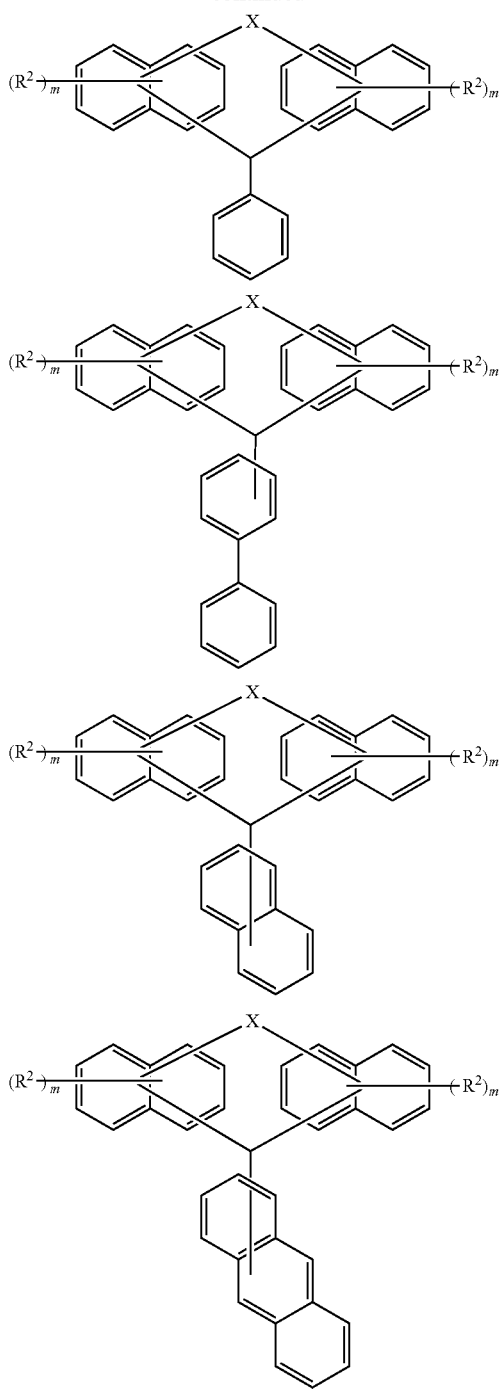
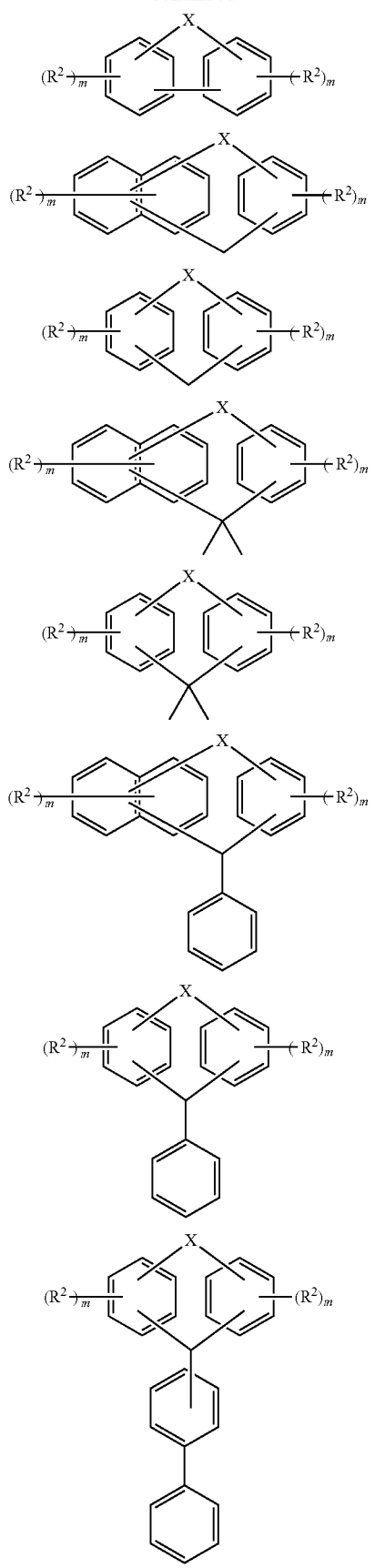
In the above formulae, $R^2$, X, and m are the same as defined in the formula (1).

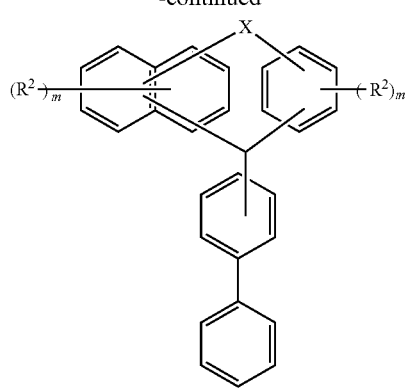
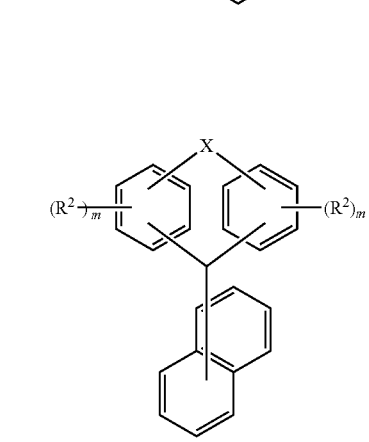
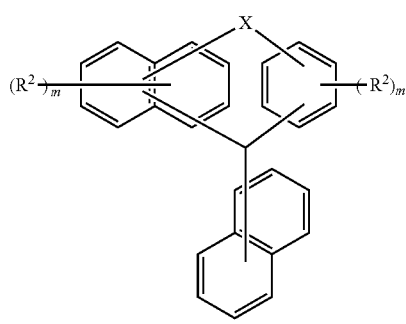
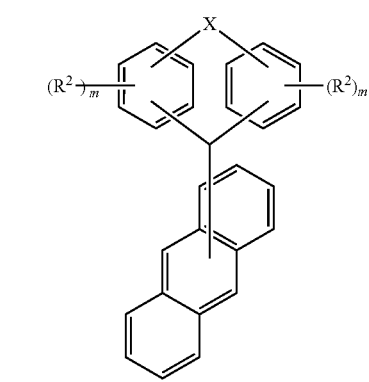
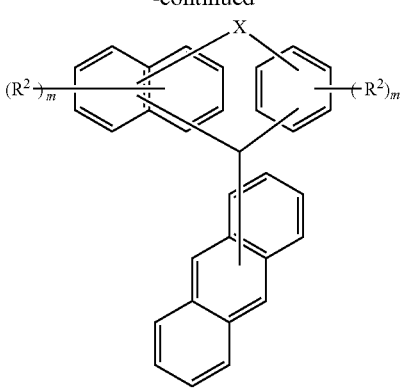
In the above formulae, $R^2$, X and m are the same as defined in the formula (1).
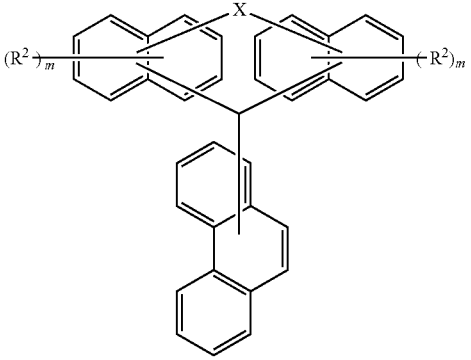
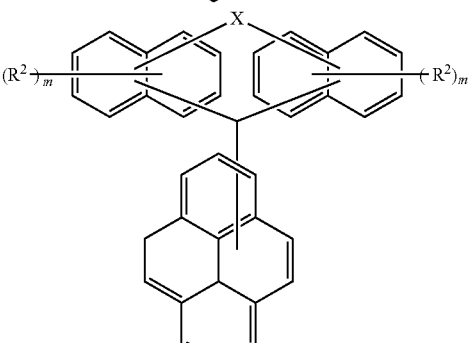
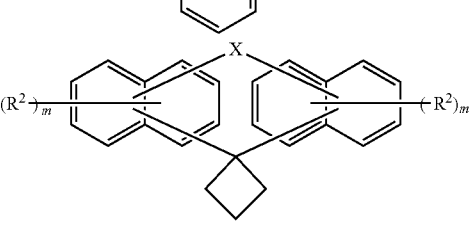
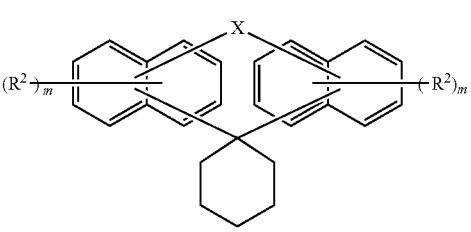

-continued
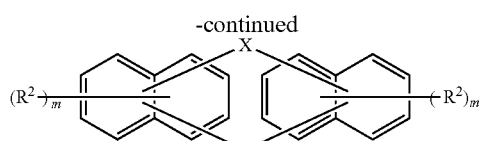
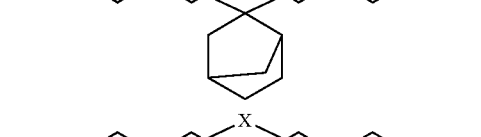
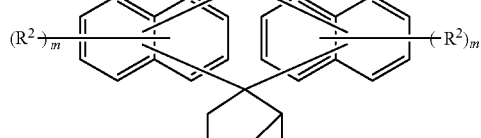
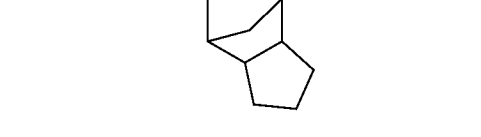
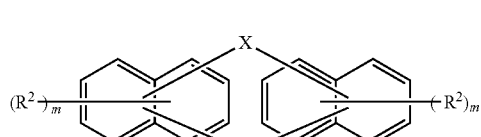
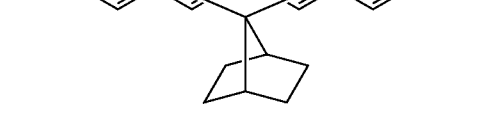
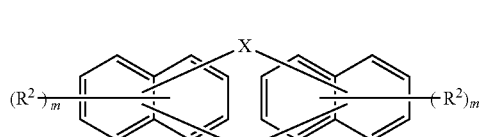
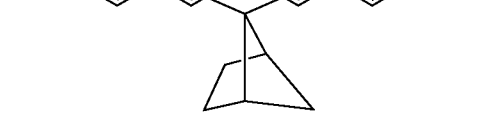
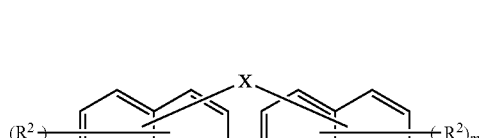
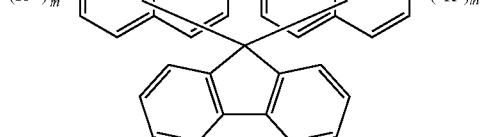
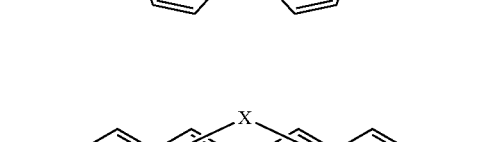
In the above formulae, $R^2$, X and m are the same as defined in the formula (1).

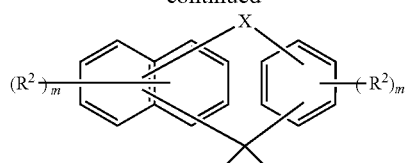
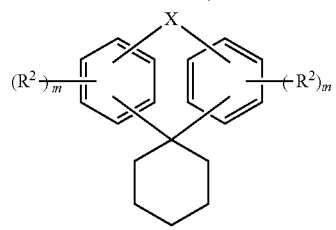
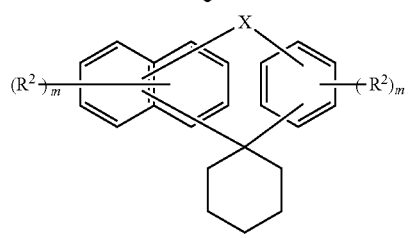
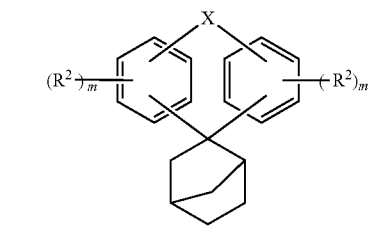
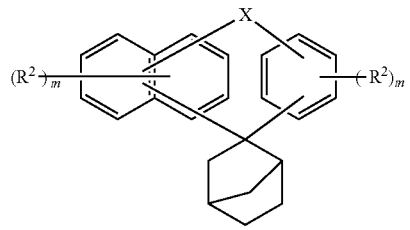
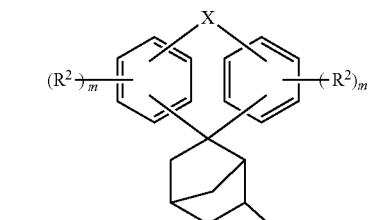
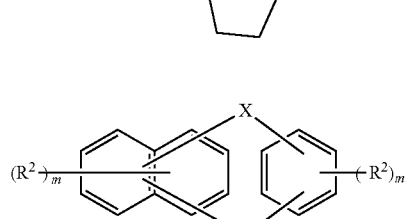
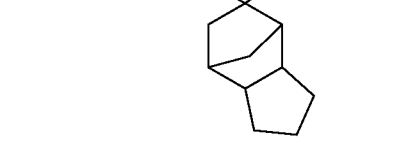
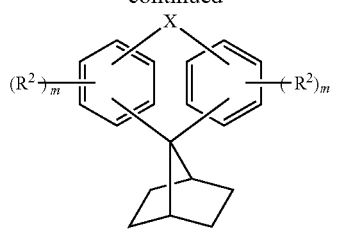
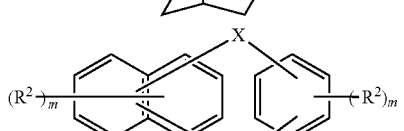
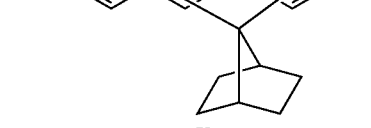
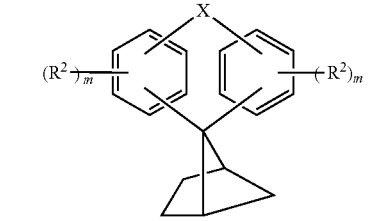
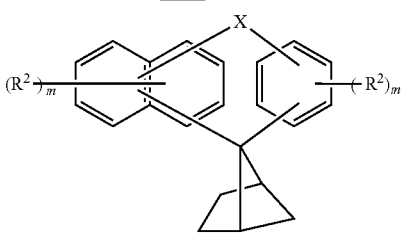
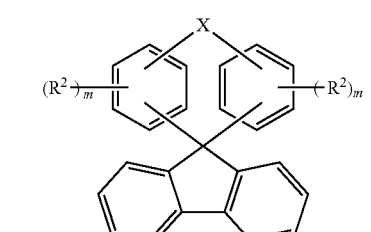
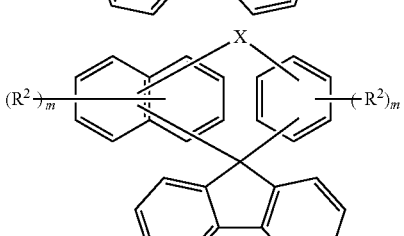
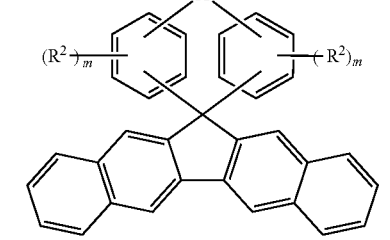

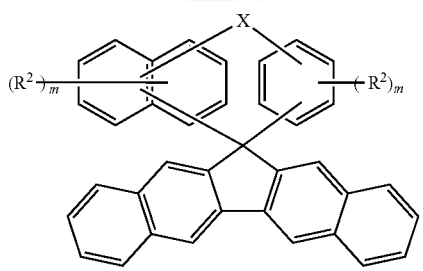
In the above formulae, R², X and m are the same as defined in the formula (1).
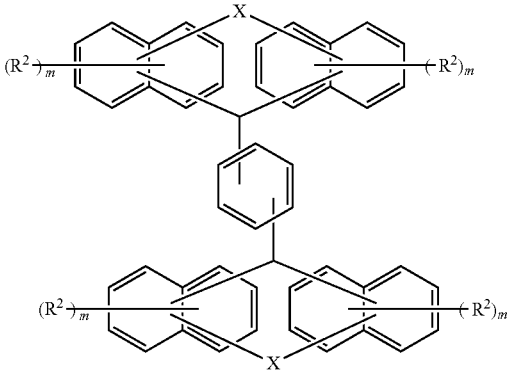
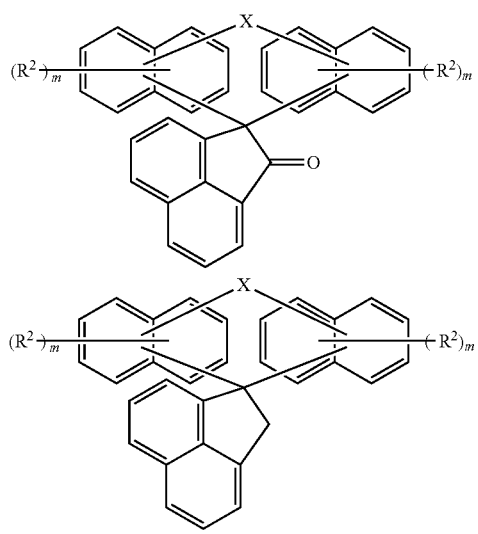
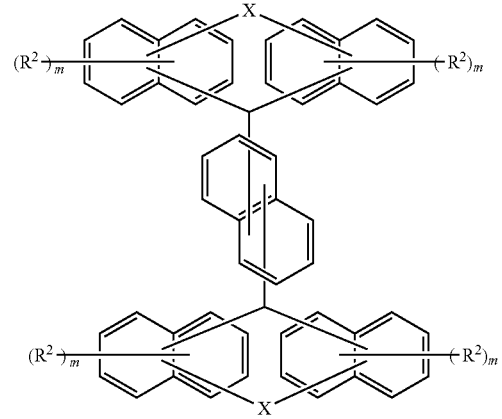
In the above formulae, R², X and m are the same as defined in the formula (1).
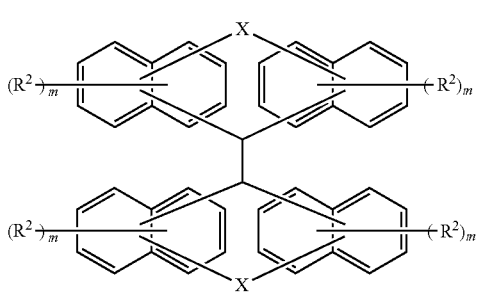
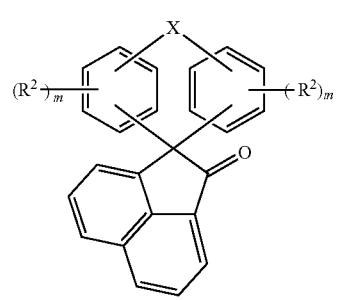
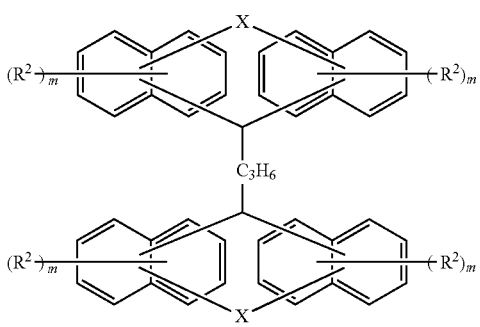
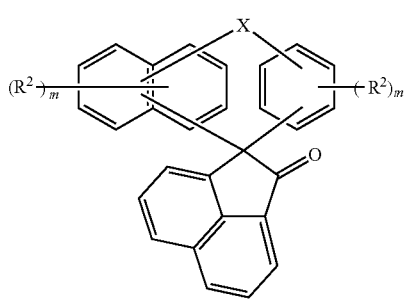

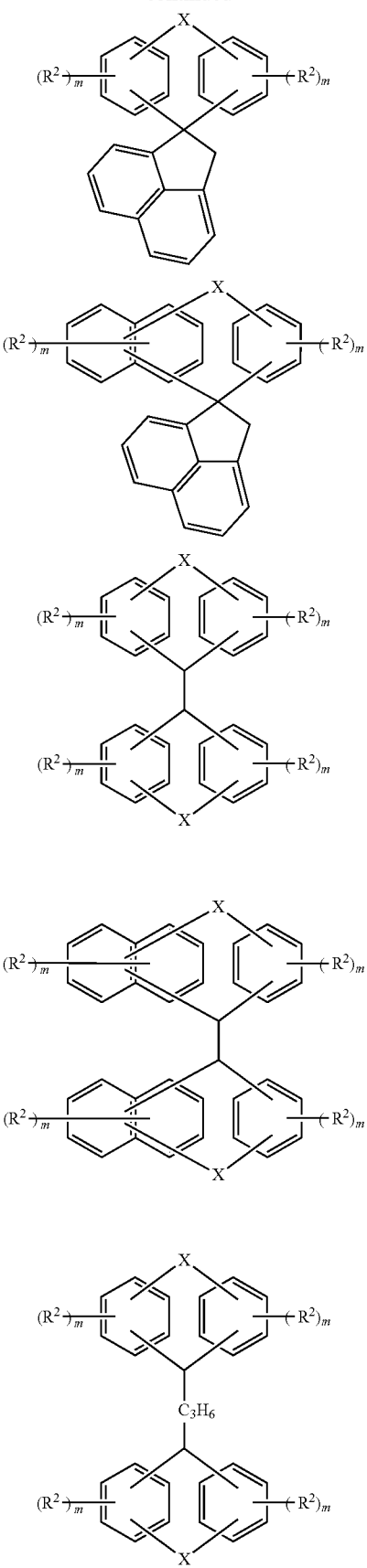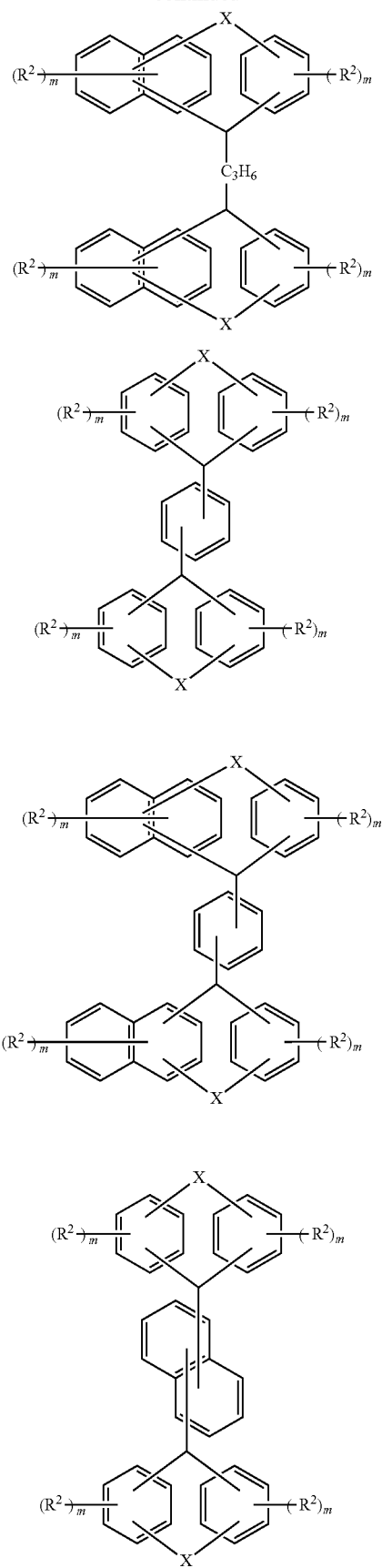

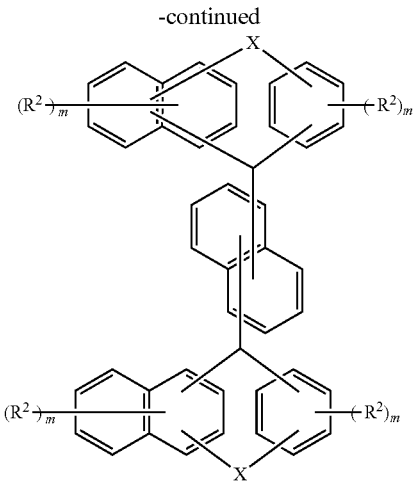
In the above formulae, $R^2$, X and m are the same as defined in the formula (1).
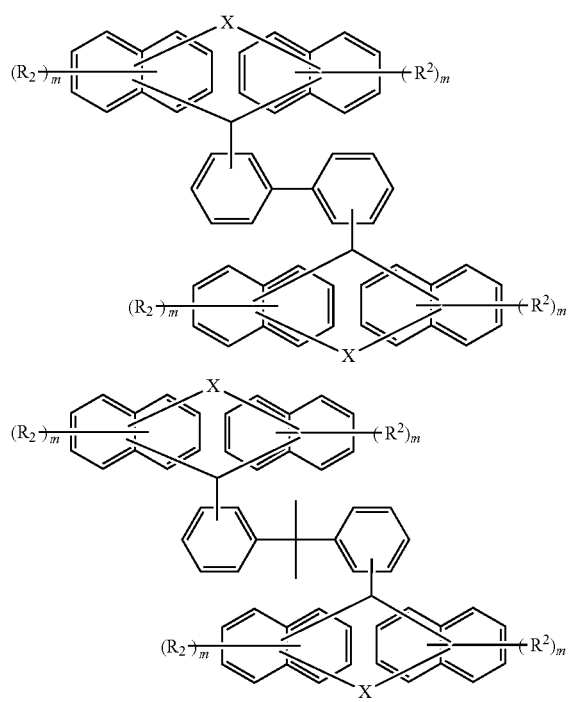
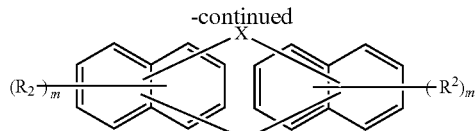
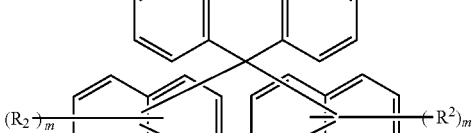
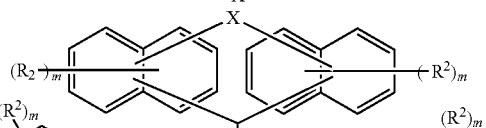
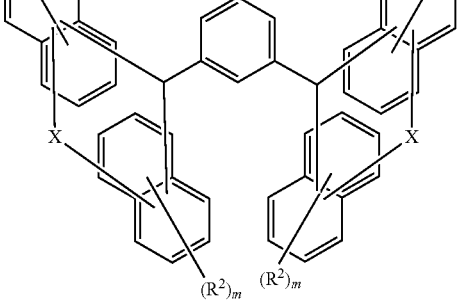
In the above formulae, $R^2$, X and m are the same as defined in the formula (1).
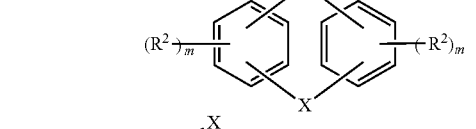
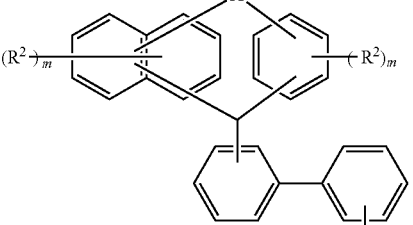
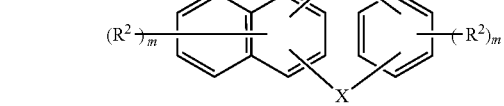

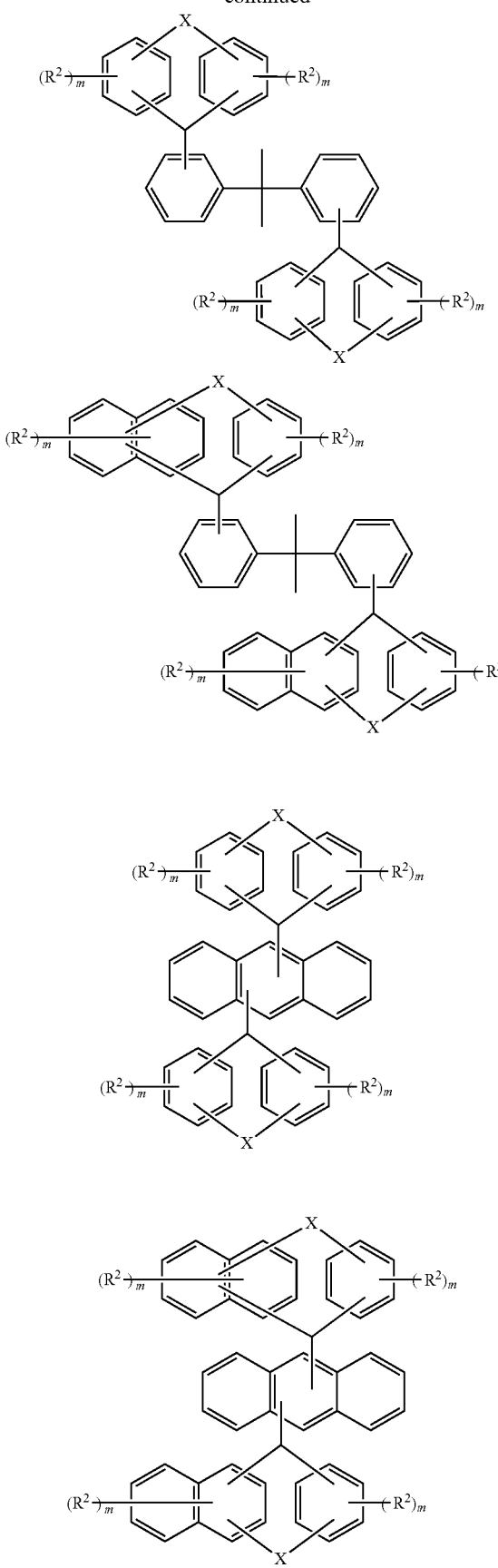
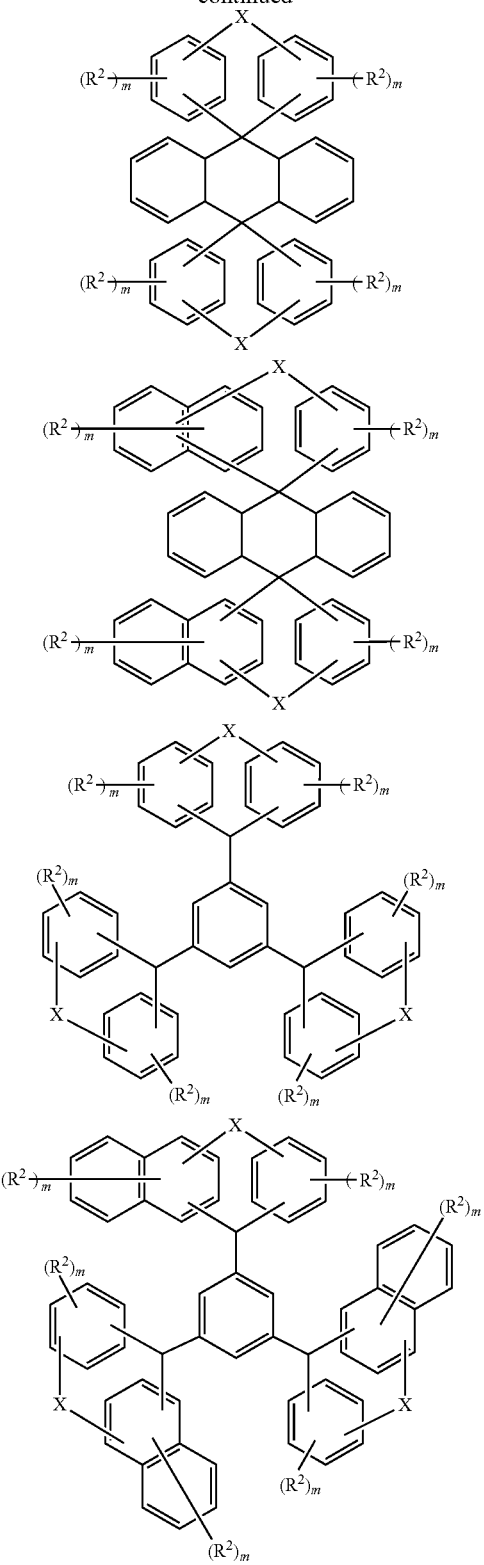
In the above formulae, $R^2$, X and m are the same as defined in the formula (1).
Specific examples of the compound represented by the formula (1) further include the following, but not limited to those exemplified herein.

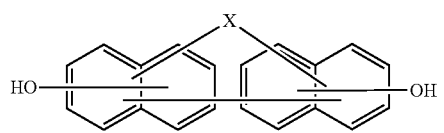
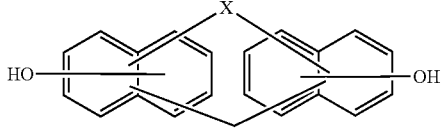
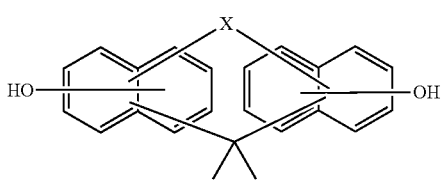
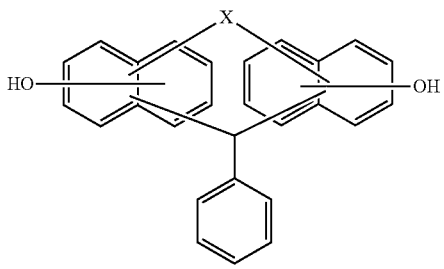
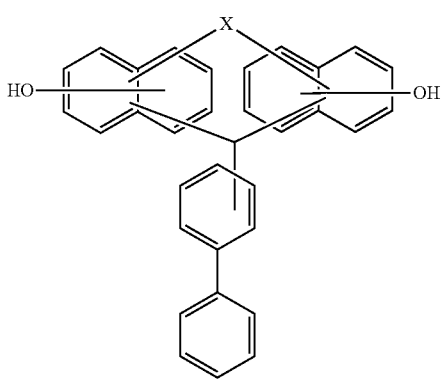
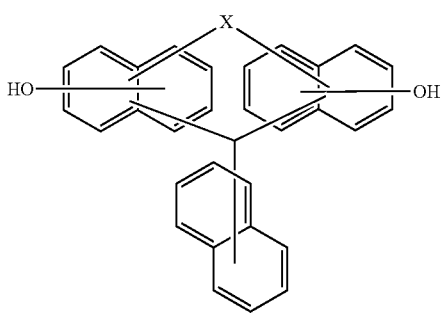
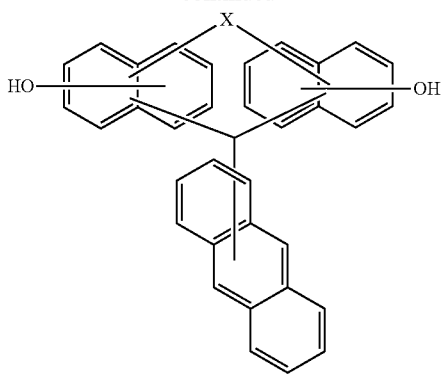
In the above formulae, X is the same as defined in the formula (1).
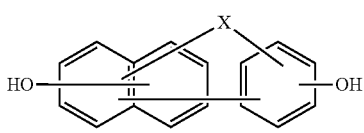
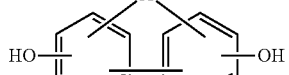
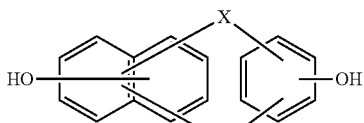
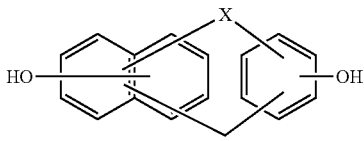
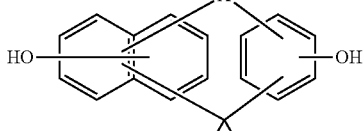
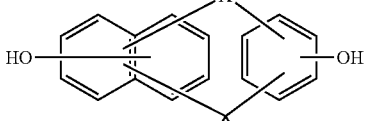
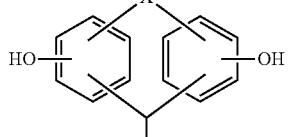

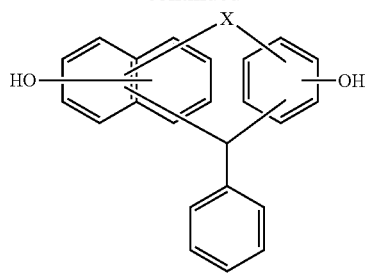
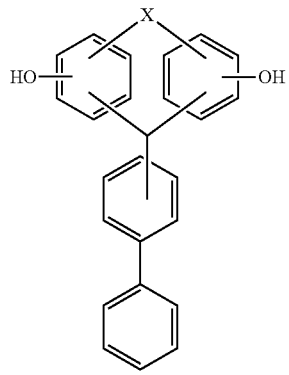
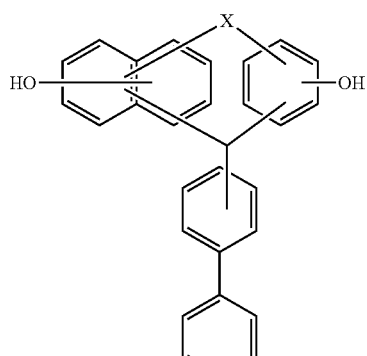
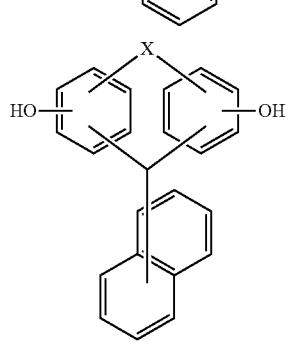
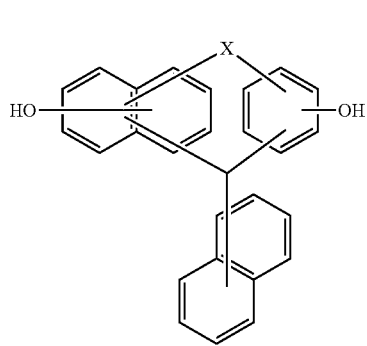
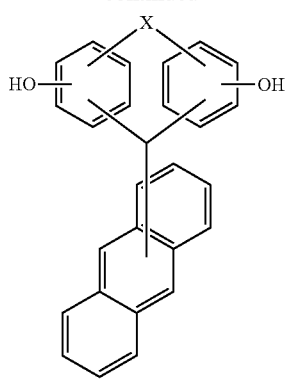
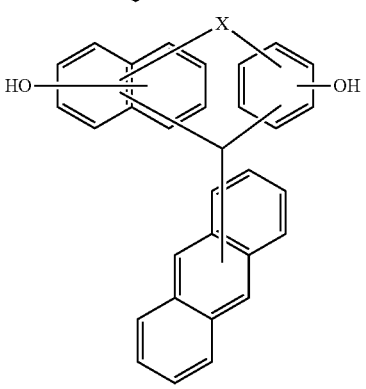
In the above formulae, X is the same as defined in the formula (1).
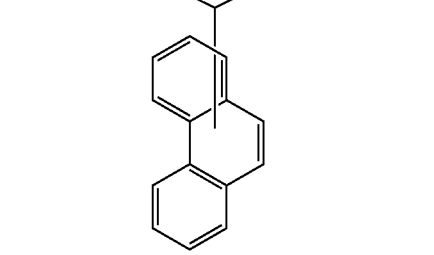
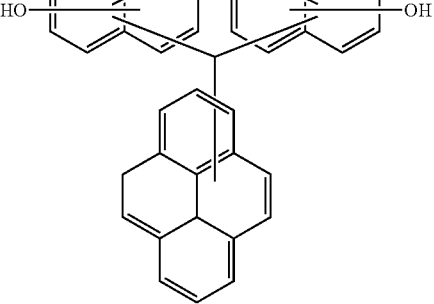

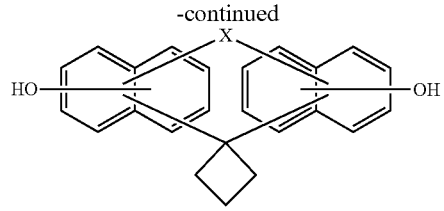
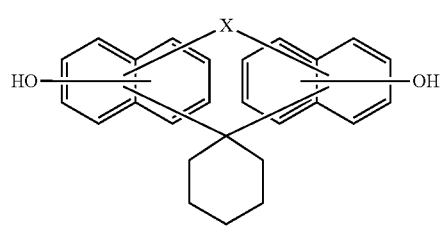
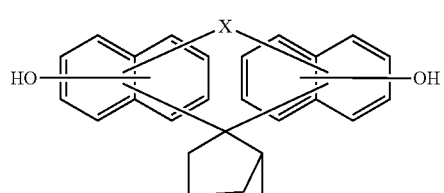
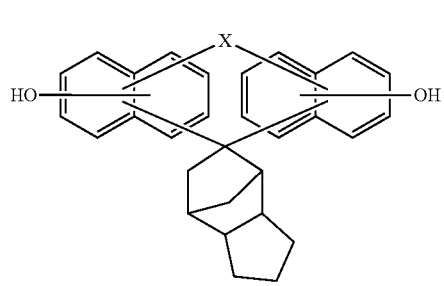
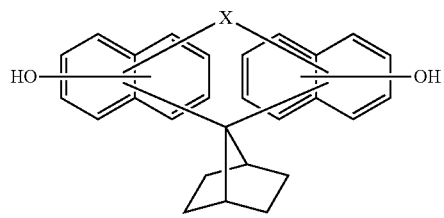
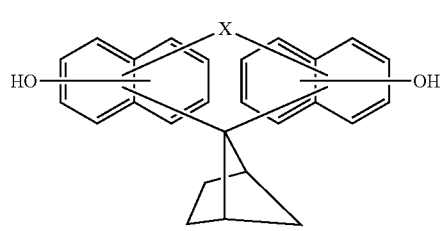
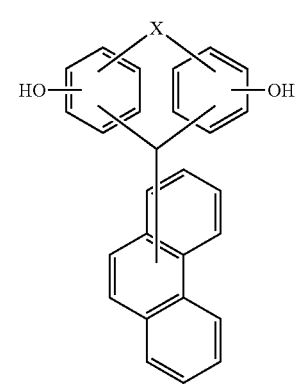
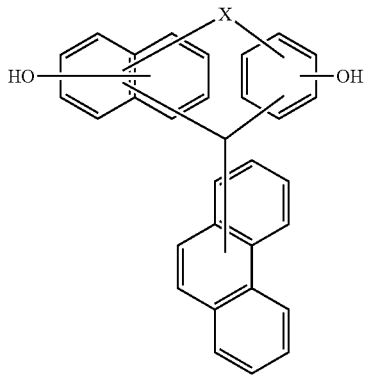
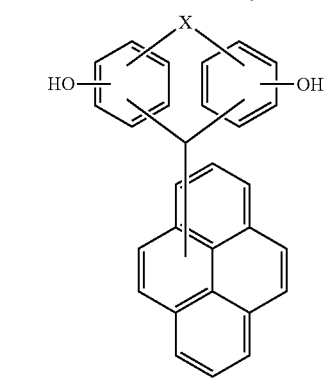
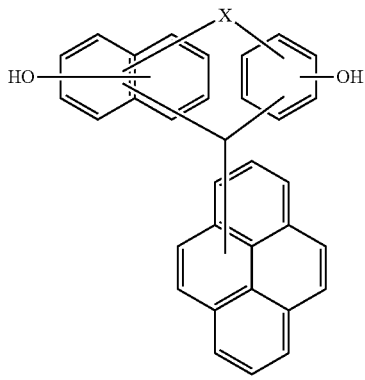
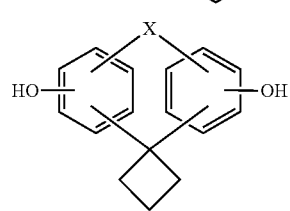
In the above formulae, X is the same as defined in the formula (1).

-continued
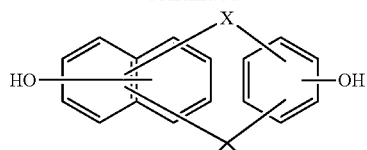
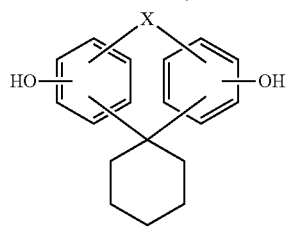
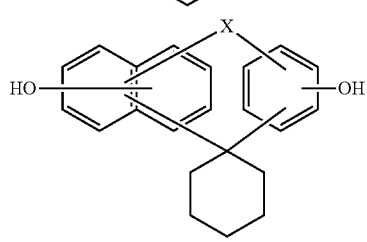
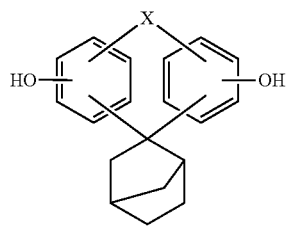
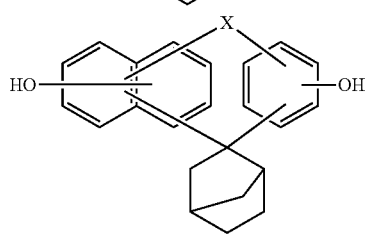
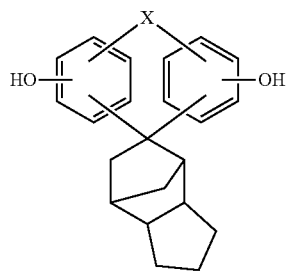
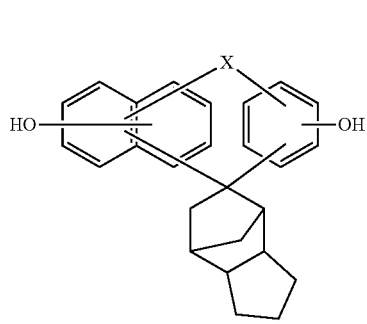
-continued
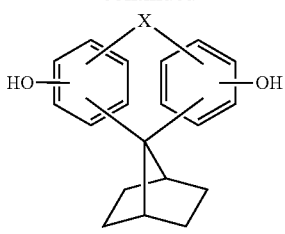
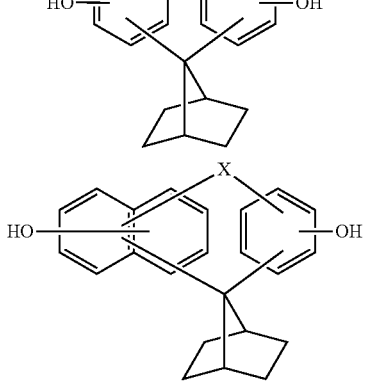
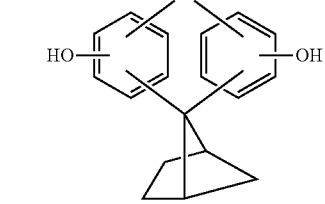
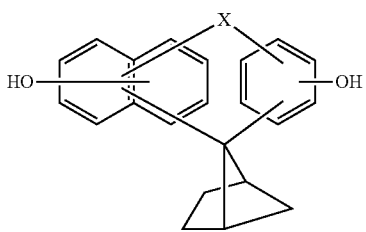
In the above formulae, X is the same as defined in the formula (1).
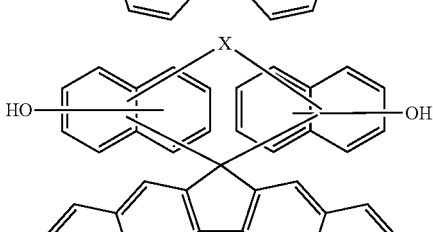
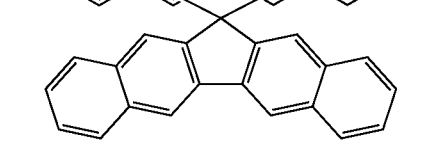

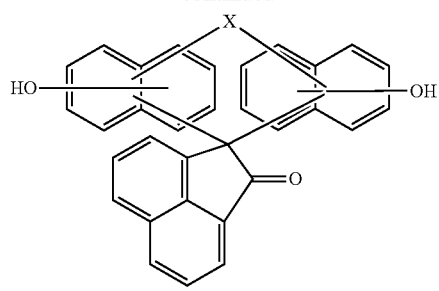
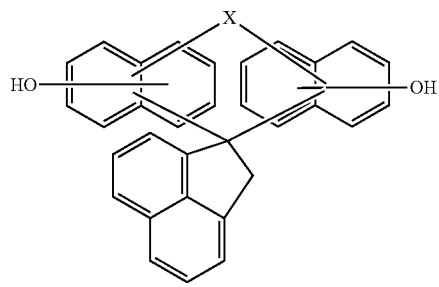
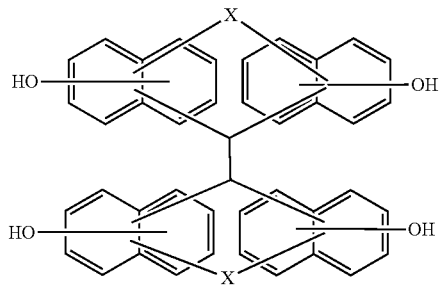
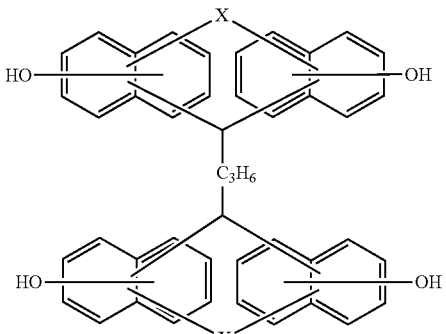
In the above formulae, X is the same as defined in the formula (1).
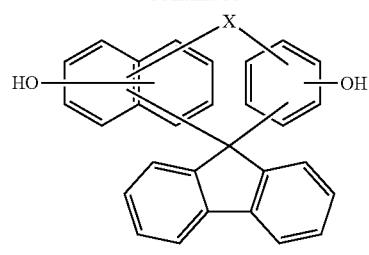
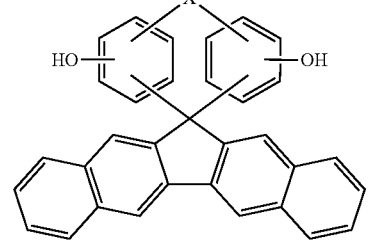
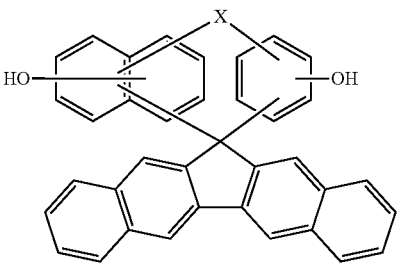
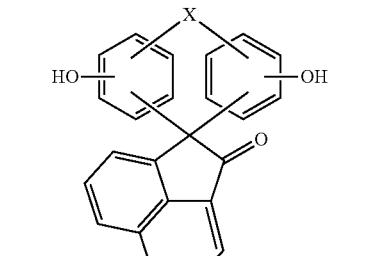
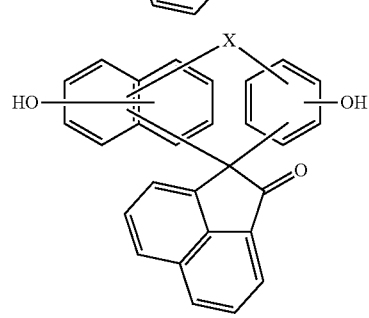
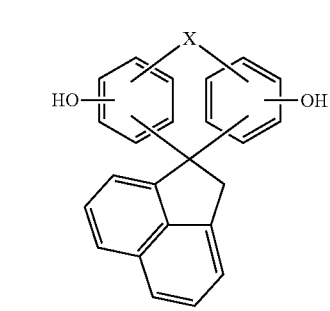

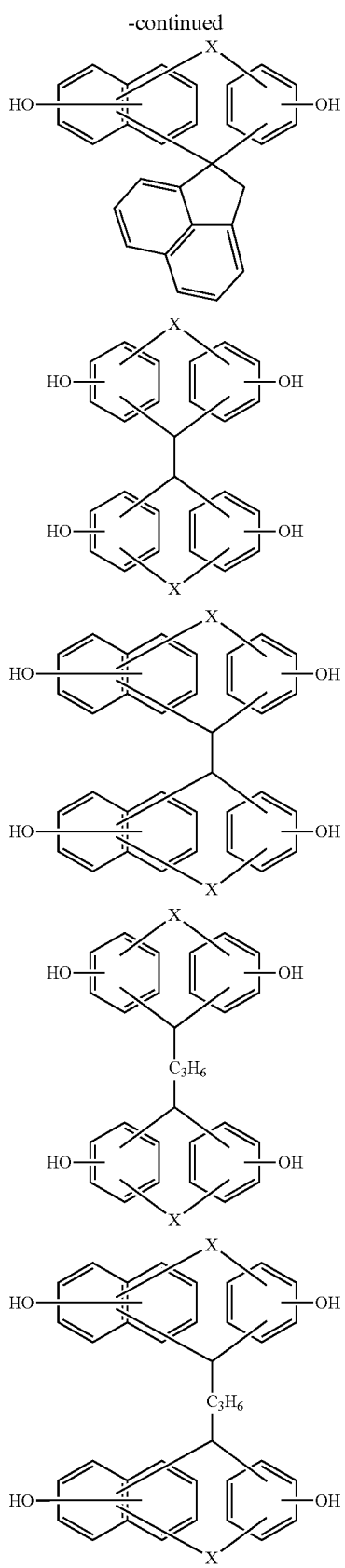
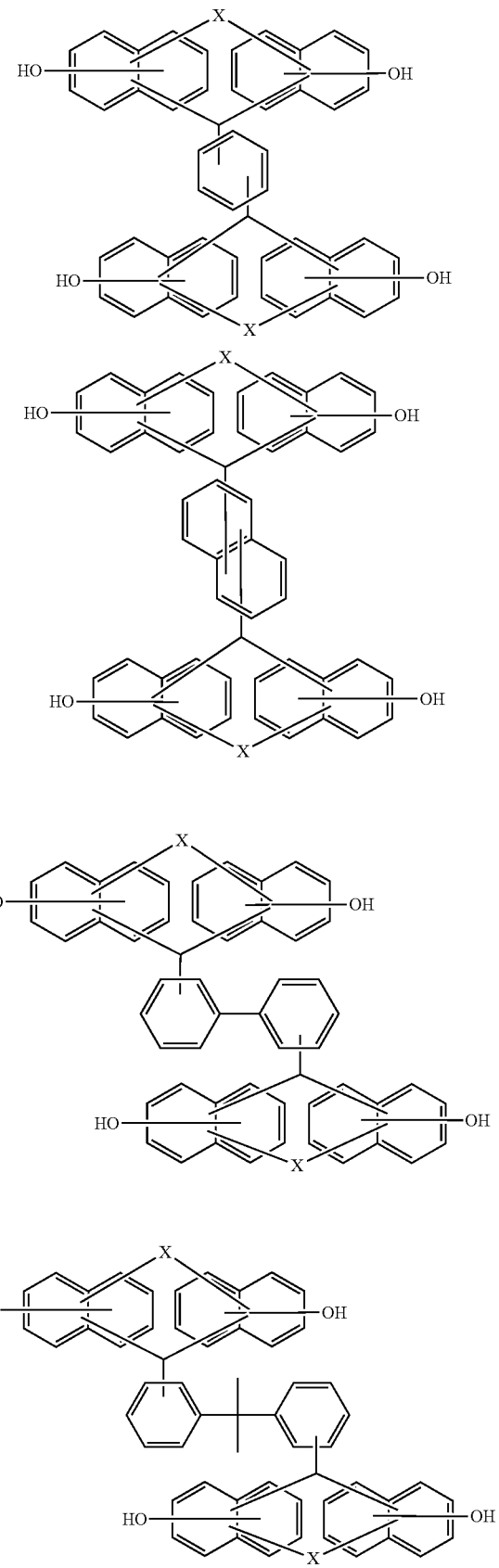
In the above formulae, X is the same as defined in the formula (1).

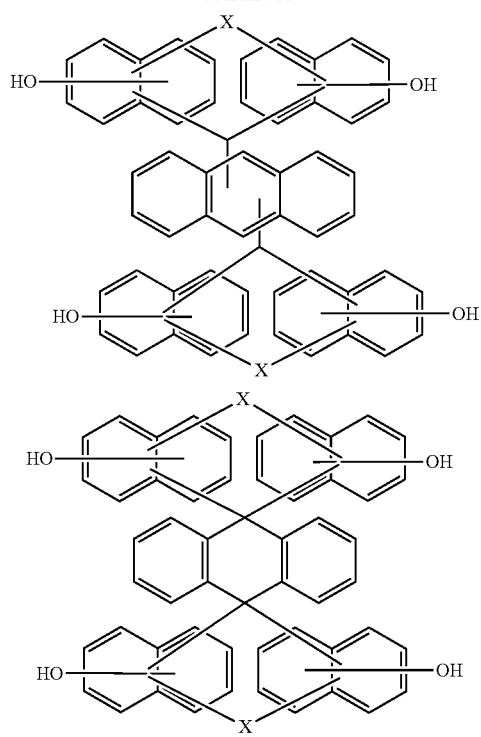
In the above formulae, X is the same as defined in the formula (1).
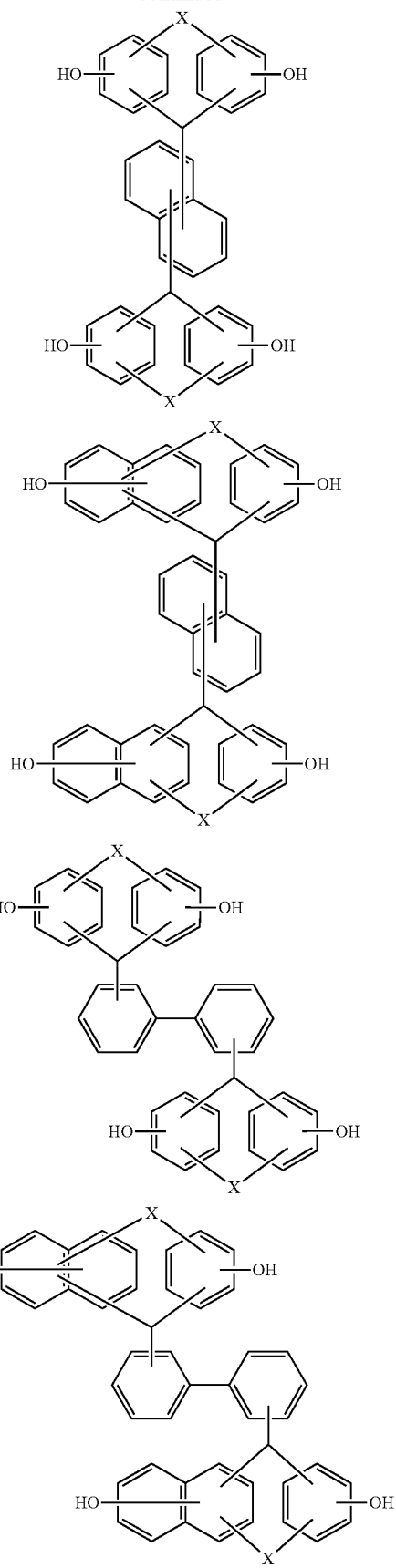

-continued
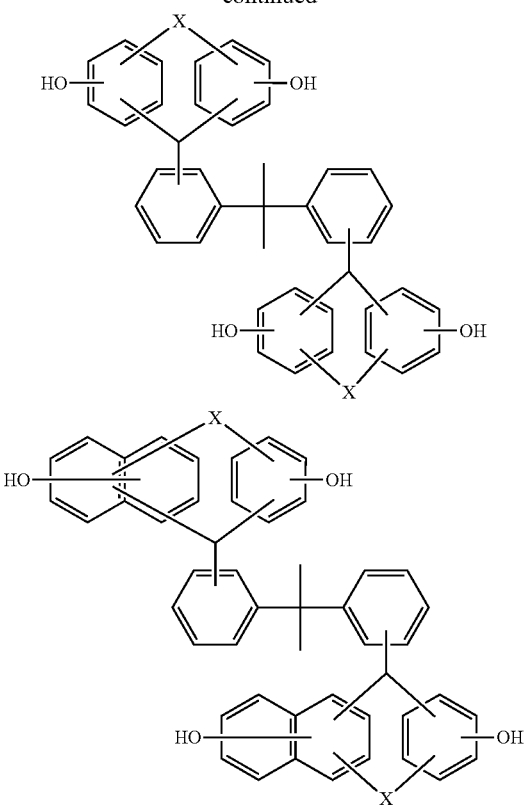
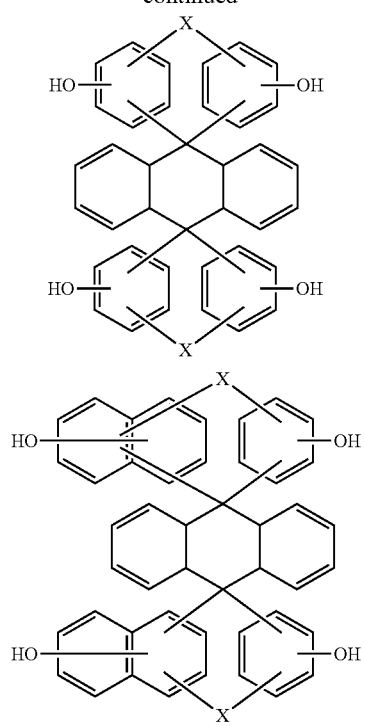
In the above formulae, X is the same as defined in the formula (1).
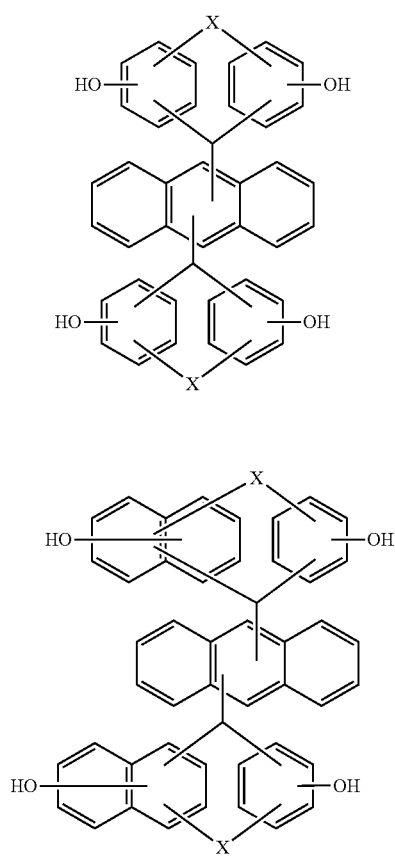
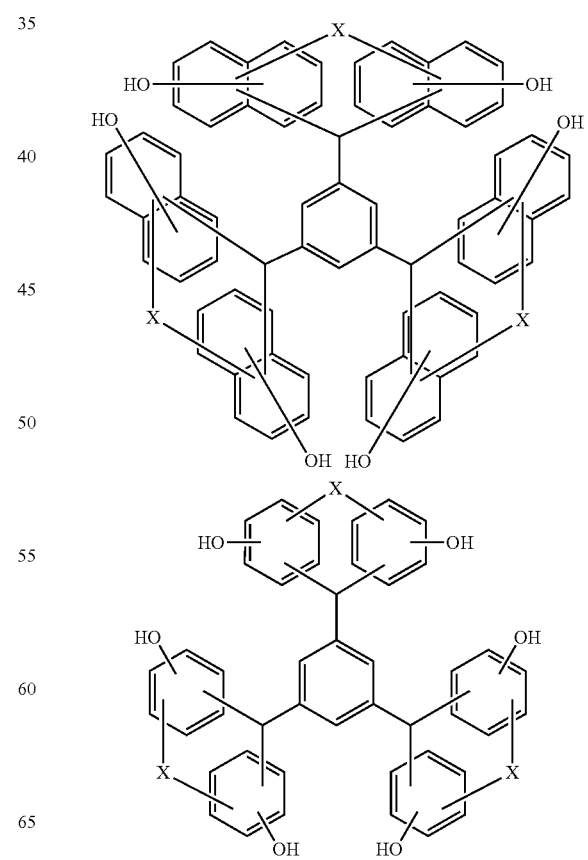

-continued

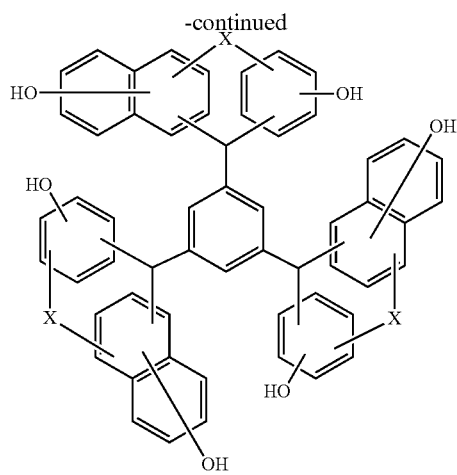

In the above formulae, X is the same as defined in the formula (1).

The compound represented by the formula (1) for use in the present embodiment can be appropriately synthesized by applying a known method, and a synthesis method thereof is not particularly limited. For example, phenols, thiophenols, naphthols or thionaphthols and the corresponding aldehydes or ketones can be subjected to a polycondensation reaction under ordinary pressure in the presence of an acid catalyst to thereby provide the compound represented by the formula (1). The reaction can also be performed under pressure, if necessary.

Examples of the phenols include phenol, methylphenol, methoxybenzene, catechol, resorcinol, hydroquinone and trimethylhydroquinone, but are not particularly limited thereto. These can be used alone, or two or more thereof can be used in combination. Among them, hydroquinone or trimethylhydroquinone is preferably used from the viewpoint of being capable of easily making a xanthene structure.

Examples of the thiophenols include benzenethiol, methylbenzenethiol, methoxybenzenethiol, benzenedithiol and trimethylbenzenedithiol, but are not particularly limited thereto. These can be used alone, or two or more thereof can be used in combination. Among them, benzenedithiol or trimethylbenzenedithiol is preferably used from the viewpoint of being capable of easily making a thioxanthene structure.

Examples of the naphthols include naphthol, methylnaphthol, methoxynaphthol, and naphthalenediol, but are not particularly limited thereto. These can be used alone, or two or more thereof can be used in combination. Among them, naphthalenediol is preferably used from the viewpoint of being capable of easily making a benzoxanthene structure.

Examples of the thionaphthols include naphthalenethiol, methyl naphthalenethiol, methoxy naphthalenethiol, and naphthalenedithiol, but are not particularly limited thereto. These can be used alone, or two or more thereof can be used in combination. Among them, naphthalenedithiol is preferably used from the viewpoint of being capable of easily making a thiobenzoxanthene structure.

The aldehydes are not particularly limited, and for example, formaldehyde, trioxane, paraformaldehyde, acetaldehyde, propylaldehyde, butylaldehyde, hexylaldehyde, decylaldehyde, undecylaldehyde, phenylacetaldehyde, phenylpropylaldehyde, furfural, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, benzaldehyde, hydroxybenzaldehyde, fluorobenzaldehyde, chlorobenzaldehyde, nitrobenzaldehyde, methylbenzaldehyde, dimethylbenzaldehyde, ethylbenzaldehyde, propylbenzaldehyde, butylbenzaldehyde, cyclohexylbenzaldehyde, biphenylaldehyde, naphthaldehyde, anthracenecarboxaldehyde, phenanthrenecarboxaldehyde, pyrenecarboxaldehyde, glyoxal, glutaraldehyde, phthalaldehyde, naphthalenedicarboxaldehyde, biphenyldicarboxaldehyde, anthracenedicarboxaldehyde, bis(diformylphenyl)methane, bis(diformylphenyl)propane or benzenetricarboxaldehyde is preferably used from the viewpoint of imparting high heat resistance.

Examples of the ketones include acetone, methyl ethyl ketone, cyclobutanone, cyclopentanone, cyclohexanone, norbornanone, tricyclohexanone, tricyclodecanone, adamantanone, fluorenone, benzofluorenone, acenaphthenequinone, acenaphthenone, and anthraquinone, but are not particularly limited thereto. These can be used alone, or two or more thereof can be used in combination. Among them, cyclopentanone, cyclohexanone, norbornanone, tricyclohexanone, tricyclodecanone, adamantanone, fluorenone, benzofluorenone, acenaphthenequinone, acenaphthenone, or anthraquinone is preferably used from the viewpoint of imparting a high heat resistance.

The acid catalyst for use in the above reaction can be appropriately selected from known ones and used, and is not particularly limited. Such an acid catalyst is an inorganic acid or an organic acid, as widely known, and examples thereof include inorganic acids such as hydrochloric acid, sulfuric acid, phosphoric acid, hydrobromic acid, or hydrofluoric acid, organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, or naphthalenedisulfonic acid, Lewis acids such as zinc chloride, aluminum chloride, iron chloride, or boron trifluoride, and solid acids such as tungstosilicic acid, tungstophosphoric acid, silicomolybdic acid, or phosphomolybdic acid, but are not particularly limited thereto. Among them, organic acids and solid acids are preferable in terms of production, and hydrochloric acid or sulfuric acid is preferably used in terms of production such as availability or handleability. Herein, these acid catalysts can be used alone, or two or more thereof can be used in combination. In addition, the amount of the acid catalyst to be used can be appropriately set depending on the types of raw materials to be used and the catalyst to be used, reaction conditions, and the like, and is not particularly limited, but the amount is preferably 0.01 to 100 parts by mass based on 100 parts by mass of reaction raw materials.

A reaction solvent may also be used during the above reaction. The reaction solvent that can be used is not particularly limited and is appropriately selected from known ones as long as the reaction of the aldehydes or ketones to be used and the phenols, thiophenols, naphthols or thionaphthols to be used progresses. Examples thereof include water, methanol, ethanol, propanol, butanol, tetrahydrofuran, dioxane, ethylene glycol dimethyl ether, ethylene glycol diethyl ether, and a mixed solvent thereof. Herein, these solvents can be used alone, or two or more thereof can be used in combination. In addition, the amount of the solvent to be used can be appropriately set depending on the types of raw materials to be used and the catalyst to be used, reaction conditions, and the like, and is not particularly limited, but the amount is preferably 0 to 2000 parts by mass based on 100 parts by mass of reaction raw materials. Furthermore, the reaction temperature in the above reaction can be appropriately selected depending on the reactivity of reaction raw materials, and is not particularly limited, but the reaction temperature usually ranges from 10 to 200° C.

In order to obtain the compound represented by the general formula (1) of the present embodiment, the reaction temperature is preferably high, and specifically, preferably ranges from 60 to 200° C. Herein, the reaction method that can be used is appropriately selected from known methods and is not particularly limited, but examples thereof include a method in which the phenols, the thiophenols, the naphthols or the thionaphthols, the aldehydes or the ketones, and the catalyst are charged at once, and a method in which the phenols, the thiophenols, the naphthols or the thionaphthols and the aldehydes or the ketones are dropped in the presence of the catalyst. After completion of the polycondensation reaction, the resulting compound can be isolated according to an ordinary method, and the isolation method is not particularly limited. For example, in order to remove the unreacted raw materials, the catalyst, and the like present in the system, a common method in which the temperature in a reaction tank is raised to 130 to 230° C. to remove the volatile component at about 1 to 50 mmHg can be adopted to thereby provide the compounds as the raw materials.

The reaction progresses under such a preferable reaction condition that 1 mol to an excess amount of the phenols, thiophenols, naphthols or thionaphthols and 0.001 to 1 mol of the acid catalyst are used based on 1 mol of the aldehydes or ketones and are reacted at ordinary pressure and at 50 to 150° C. for about 20 minutes to 100 hours.

After completion of the reaction, the compounds as the raw materials can be isolated by a known method. For example, the compound represented by the general formula (1) as the raw material, can be obtained by concentrating a reaction solution, adding pure water thereto to precipitate a reaction product, cooling the resultant to room temperature followed by filtration for separation, drying a solid obtained by filtration, then separating the solid into the reaction product and a by-product for purification by column chromatography, and performing distilling off of the solvent, filtration and drying.

The resin for use in the present embodiment is the resin having a structure represented by the formula (2).

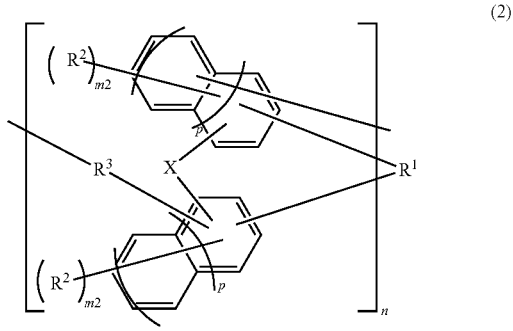

(2)

In the formula (2), each X independently represents an oxygen atom or a sulfur atom. $R^1$ represents a single bond or a 2n-valent hydrocarbon group having 1 to 30 carbon atoms, and the hydrocarbon group optionally has a cyclic hydrocarbon group, a double bond, a hetero atom, or an aromatic group having 6 to 30 carbon atoms. Each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group. Herein, at least one $R^2$ represents a hydroxyl group. Each $R^3$ independently represents a single bond, or a linear or branched alkylene group having 1 to 20 carbon atoms. Each $m^2$ is independently an integer of 1 to 5, and n is an integer of 1 to 4. Each p is independently 0 or 1. Herein, the 2n-valent hydrocarbon group is the same as defined in the formula (1).

The resin having a structure represented by the formula (2) for use in the present embodiment is obtained by, for example, reacting the compound represented by the formula (1) with a monomer having crosslinking reactivity.

The monomer having crosslinking reactivity is not particularly limited as long as the one enables to form an oligomer or polymer of the compound represented by the formula (1), and various known ones can be used. Specific examples thereof include aldehyde, ketone, carboxylic acid, carboxylic halide, a halogen-containing compound, an amino compound, an imino compound, isocyanate, and an unsaturated hydrocarbon group-containing compound, but are not limited thereto.

Specific examples of the resin having a structure represented by formula (2) include, but not limited to the following, a novolac resin obtained by a condensation reaction of the compound represented by the formula (1) with an aldehyde as the monomer having crosslinking reactivity, or the like.

Herein, examples of the aldehyde for use in forming the novolac resin of the compound represented by the formula (1) include formaldehyde, trioxane, paraformaldehyde, benzaldehyde, acetaldehyde, propylaldehyde, phenylacetaldehyde, phenylpropylaldehyde, hydroxybenzaldehyde, chlorobenzaldehyde, nitrobenzaldehyde, methylbenzaldehyde, ethylbenzaldehyde, butylbenzaldehyde, biphenylaldehyde, naphthaldehyde, anthracenecarbaldehyde, phenanthrenecarbaldehyde, pyrenecarbaldehyde, and furfural, but are not limited thereto. Among them, formaldehyde is preferable. Herein, these aldehydes can be used alone, or two or more thereof can be used in combination. In addition, the amount of the aldehydes to be used is not particularly limited, but the amount is preferably 0.2 to 5 mol and more preferably 0.5 to 2 mol, based on 1 mol of the compound represented by the formula (1).

A catalyst can also be used in the condensation reaction of the compound represented by the formula (1) with an aldehyde. The acid catalyst that can be used herein is appropriately selected from known ones, and is not particularly limited. Such an acid catalyst is an inorganic acid or an organic acid, as widely known, and examples thereof include inorganic acids such as hydrochloric acid, sulfuric acid, phosphoric acid, hydrobromic acid, or hydrofluoric acid, organic acids such as oxalic acid, malonic acid, succinic acid, adipic acid, sebacic acid, citric acid, fumaric acid, maleic acid, formic acid, p-toluenesulfonic acid, methanesulfonic acid, trifluoroacetic acid, dichloroacetic acid, trichloroacetic acid, trifluoromethanesulfonic acid, benzenesulfonic acid, naphthalenesulfonic acid, or naphthalenedisulfonic acid, Lewis acids such as zinc chloride, aluminum chloride, iron chloride, or boron trifluoride, and solid acids such as tungstosilicic acid, tungstophosphoric acid, silicomolybdic acid, or phosphomolybdic acid, but are not limited thereto. Among them, organic acids and solid acids are preferable in terms of production, and hydrochloric acid or sulfuric acid is preferably used in terms of production such as availability or handleability. Herein, these acid catalysts can be used alone, or two or more thereof can be used in combination. In addition, the amount of the acid catalyst to be used can be appropriately set depending on the types of raw materials to be used and the catalyst to be used, reaction conditions, and the like, and is not particularly limited, but the amount is preferably 0.01 to 100 parts by mass based on 100 parts by mass of reaction raw materials. However, in the case of copolymerization with a compound having a non-conjugated double bond, such as indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, 5-vinylnorborna-2-ene, α-pinene, β-pinene, and limonene, the aldehydes are not necessarily required.

A reaction solvent can also be used in the condensation reaction of the compound represented by the formula (1) with an aldehyde. The reaction solvent in the polycondensation, which can be used, is appropriately selected from known ones, and is not particularly limited, but examples thereof include water, methanol, ethanol, propanol, butanol, tetrahydrofuran, dioxane, and a mixed solvent thereof. Herein, these reaction solvents can be used alone, or two or more thereof can be used in combination. In addition, the amount of the reaction solvent to be used can be appropriately set depending on the types of raw materials to be used and the catalyst to be used, reaction conditions, and the like, and is not particularly limited, but the amount preferably ranges from 0 to 2000 parts by mass based on 100 parts by mass of reaction raw materials. Furthermore, the reaction temperature can be appropriately selected depending on the reactivity of reaction raw materials, and is not particularly limited, but the reaction temperature usually ranges from 10 to 200° C. Herein, the reaction method that can be used is appropriately selected from known methods, and is not particularly limited, but examples thereof includes a method in which the compound represented by the general formula (1), the aldehydes, and the catalyst are charged at once, and a method in which the compound represented by the general formula (1) and the aldehydes are dropped in the presence of the catalyst. After completion of the polycondensation reaction, the resulting compound can be isolated according to an ordinary method, and the isolation method is not particularly limited. For example, in order to remove the unreacted raw materials and the catalyst present in the system, a common method in which the temperature in a reaction tank is raised to 130 to 230° C. to remove a volatile component at about 1 to 50 mmHg can be adopted to thereby provide a novolac resin as the raw material.

Herein, the resin having a structure represented by the formula (2) may be a homopolymer of the compound represented by the formula (1), or may be a copolymer of the compound represented by the formula (1) with other phenols. Examples of the copolymerizable phenols include phenol, cresol, dimethylphenol, trimethylphenol, butylphenol, phenylphenol, diphenylphenol, naphthylphenol, resorcinol, methylresorcinol, catechol, butylcatechol, methoxyphenol, methoxyphenol, propylphenol, pyrogallol, and thymol, but are not limited thereto.

In addition, the resin having a structure represented by the formula (2) may be one obtained by copolymerization with a polymerizable monomer other than the above-described other phenols. Examples of such a copolymerizable monomer include naphthol, methylnaphthol, methoxynaphthol, dihydroxynaphthalene, indene, hydroxyindene, benzofuran, hydroxyanthracene, acenaphthylene, biphenyl, bisphenol, trisphenol, dicyclopentadiene, tetrahydroindene, 4-vinylcyclohexene, norbornadiene, vinylnorbornaene, pinene, and limonene, but are not limited thereto. Herein, the resin having a structure represented by the general formula (2) may be a bi or higher functional (for example, bi to tetra) copolymer of the compound represented by the general formula (1) with the above-described phenols, a bi or higher functional (for example, bi to tetra) copolymer of the compound represented by the general formula (1) with the above-described copolymerizable monomer, or a ter or higher (for example, ter to tetra) copolymer of the compound represented by the general formula (1), the above-described phenols and the above-described copolymerizable monomer.

The compound represented by the formula (1) or the resin having a structure represented by the formula (2) for use in the present embodiment may be used alone, or can also be used as a mixture of two or more. The compound represented by the formula (1) or the resin having a structure represented by the formula (2) may contain various surfactants, various crosslinking agents, various acid generators, various stabilizers, and the like.

In the present embodiment, the organic solvent optionally immiscible with water means an organic solvent having a solubility in water at room temperature, of less than 30%. The organic solvent optionally immiscible with water is not particularly limited, but is preferably an organic solvent that can be safely applied to a semiconductor manufacturing process. Herein, the solubility is preferably less than 20%, more preferably less than 10%. The amount of the organic solvent optionally immiscible with water, to be used, is not particularly limited, but can be usually about 1 to 100 times by mass based on the amount of the compound represented by the formula (1) or the resin having a structure represented by the formula (2) to be used, and is preferably 1 time by mass or more and 10 times by mass or less, more preferably 1 time by mass or more and less than 9 times by mass, further preferably 2 to 5 times by mass.

Specific examples of the solvent to be used include, but not limited to the following, ethers such as diethyl ether and diisopropyl ether, esters such as ethyl acetate, n-butyl acetate and isoamyl acetate, ketones such as methyl ethyl ketone, methyl isobutyl ketone, ethyl isobutyl ketone, cyclohexanone, cyclopentanone, 2-heptanone and 2-pentanone, glycol ether acetates such as ethylene glycol monoethyl ether acetate, ethylene glycol monobutyl ether acetate, propylene glycol monomethyl ether acetate (PGMEA) and propylene glycol monoethyl ether acetate, aliphatic hydrocarbons such as n-hexane and n-heptane, aromatic hydrocarbons such as toluene and xylene, and halogenated hydrocarbons such as methylene chloride and chloroform. Among them, toluene, 2-heptanone, cyclohexanone, cyclopentanone, methyl isobutyl ketone, propylene glycol monomethyl ether acetate, ethyl acetate, and the like are preferable, methyl isobutyl ketone, ethyl acetate, cyclohexanone, propylene glycol monomethyl ether acetate, and the like are more preferable, and methyl isobutyl ketone and ethyl acetate are further preferable. Methyl isobutyl ketone, ethyl acetate, and the like are relatively high in saturation solubility of the compound represented by the formula (1) or the resin having a structure represented by the formula (2) and are relatively low in boiling point, and therefore, when such a solvent is used, the load in the case of industrial distillation off of the solvent or in a step of removing the solvent by drying tends to be reduced.

The above solvents can be used alone or can be used as a mixture of two or more.

The acidic aqueous solution for use in the present embodiment is appropriately selected from aqueous solutions in which a commonly known organic or inorganic compound is dissolved in water. Examples thereof include, but not limited to the following, an aqueous solution in which a mineral acid such as hydrochloric acid, sulfuric acid, nitric acid or phosphoric acid is dissolved in water, and an aqueous solution in which an organic acid such as acetic acid, propionic acid, oxalic acid, malonic acid, succinic acid, fumaric acid, maleic acid, tartaric acid, citric acid, methanesulfonic acid, phenolsulfonic acid, p-toluenesulfonic acid or trifluoroacetic acid is dissolved in water. These acidic aqueous solutions can be used singly or two or more thereof can be used in combination. Among these acidic aqueous solutions, at least one aqueous solution of mineral acid selected from the group consisting of hydrochloric acid, sulfuric acid, nitric acid and phosphoric acid, or at least one aqueous solution of organic acid selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid and trifluoroacetic acid is preferable, an aqueous solution of an sulfuric acid or nitric acid, and an aqueous solution of a carboxylic acid such as acetic acid, oxalic acid, tartaric acid or citric acid are more preferable, an aqueous solution of sulfuric acid, oxalic acid, tartaric acid or citric acid is further preferable, and an aqueous solution of oxalic acid is further more preferable. It is considered that a polyvalent carboxylic acid such as oxalic acid, tartaric acid or citric acid is coordinated to a metal ion to exert the chelate effect and thus tends to effectively remove the metal. According to the object of the present embodiment, it is preferable to use, as the water used here, water having a low metal content, such as ion-exchange water.

The pH of the acidic aqueous solution for use in the present embodiment is not particularly limited, but the acidity of the aqueous solution is preferably adjusted in consideration of the influence on the compound represented by the formula (1) or the resin having a structure represented by the formula (2). The pH usually ranges from about 0 to 5, preferably about 0 to 3.

The amount of the acidic aqueous solution for use in the present embodiment, to be used, is not particularly limited, but is preferably adjusted from the viewpoints of reducing the number of extractions for metal removal and ensuring operability in consideration of the total amount of the liquid. From the viewpoints, the amount of the aqueous solution to be used is 10 to 200% by mass, preferably 20 to 100% by mass, based on the amount of the solution of the compound represented by the formula (1) or the resin having a structure represented by the formula (2) dissolved in the organic solvent.

In the present embodiment, the above acidic aqueous solution can be brought into contact with the solution including the compound represented by the formula (1) or the resin having a structure represented by the formula (2) and the organic solvent optionally immiscible with water, thereby extracting the metal component. The embodiment for such contact is not particularly limited, and for example, a known mixing method such as stirring or ultrasonic dispersion can be adopted.

In the present embodiment, the solution (A) preferably further includes an organic solvent optionally miscible with water. In the present embodiment, the organic solvent optionally miscible with water means an organic solvent having a solubility in water at room temperature, of 70% or more. The solubility of the organic solvent optionally miscible with water is preferably 80% or more, more preferably 90% or more. When the organic solvent optionally miscible with water is included, the amount of the compound represented by the formula (1) or the resin having a structure represented by the formula (2) to be charged can be increased, and there is the following tendency: liquid separation property can be enhanced to allow purification to be performed at a high pot efficiency. The method of adding the organic solvent optionally miscible with water is not particularly limited. For example, any of a method of adding such an organic solvent to the solution including the organic solvent in advance, a method of adding such an organic solvent to water or the acidic aqueous solution in advance, and a method of bringing the solution including the organic solvent into contact with water or the acidic aqueous solution and then adding such an organic solvent may be adopted. Among them, a method of adding such an organic solvent to the solution including the organic solvent in advance, is preferable in terms of operation processability and ease of management of the amount to be charged.

The organic solvent optionally miscible with water for use in the present embodiment is not particularly limited, but is preferably an organic solvent that can be safely applied to a semiconductor manufacturing process. The amount of the organic solvent optionally miscible with water to be used is not particularly limited as long as the solution phase and the aqueous phase are separated, but the organic solvent optionally miscible with water can be usually used in an amount of about 0.1 to 100 times by mass, preferably 0.1 to 10 times by mass, more preferably 0.1 to 2 times by mass, further preferably 0.5 to 2 times by mass, further more preferably 0.5 to 1.5 times by mass, based on the amount of the compound represented by the formula (1) or the resin having a structure represented by the formula (2) to be used.

Specific examples of the solvent optionally miscible with water for use in the present embodiment include, but not limited to the following, ethers such as tetrahydrofuran and 1,3-dioxolane, alcohols such as methanol, ethanol and isopropanol, ketones such as acetone and N-methylpyrrolidone, and glycol ethers such as ethylene glycol monoethyl ether, ethylene glycol monobutyl ether, propylene glycol monomethyl ether (PGME) and propylene glycol monoethyl ether. Among them, N-methylpyrrolidone, propylene glycol monomethyl ether, and the like are preferable, and N-methylpyrrolidone and propylene glycol monomethyl ether are more preferable.

These solvents can be used alone or can be used as a mixture of two or more.

In the present embodiment, the temperature in bringing of the solution (A) into contact with the acidic aqueous solution, namely, in performing of the extraction treatment usually ranges from 20 to 90° C., preferably ranges from 30 to 80° C. The extraction operation is not particularly limited, and is performed by, for example, mixing these solutions well with stirring or the like and then leaving them to still stand. Thus, the metal component, which is included in the solution including the compound represented by the formula (1) or the resin having a structure represented by the formula (2) and the organic solvent, is transferred to the aqueous phase. Such an operation can also allow for a reduction in the acidity of the solution, inhibiting the compound represented by the formula (1) or the resin having a structure represented by the formula (2) from being modified.

The resulting mixture is spontaneously separated to the solution phase including the compound represented by the formula (1) or the resin having a structure represented by the formula (2) and the organic solvent, and the aqueous phase, and therefore the solution including the compound represented by the formula (1) or the resin having a structure represented by the formula (2) and the organic solvent is recovered by decantation or the like. The standing time is not particularly limited, but the standing time is preferably adjusted from the viewpoint of more favorably separating the solution phase including the organic solvent, and the aqueous phase. The standing time is usually 1 minute or more, preferably 10 minutes or more, more preferably 30 minutes or more.

The extraction treatment may be performed only once, and is also effectively performed by repeatedly performing operations such as mixing, standing and separation a plurality of times.

In the present embodiment, after the extraction treatment by the step of bringing the solution (A) with the acidic aqueous solution is performed, a step of performing an extraction treatment with water is preferably further included. That is, after the extraction treatment is performed using the acidic aqueous solution, the solution including the compound represented by the formula (1) or the resin having a structure represented by the formula (2) and the organic solvent, which is extracted from the aqueous solution and recovered, is preferably further subjected to an extraction treatment with water. The extraction treatment with water is not particularly limited, and can be performed by, for example, well mixing with stirring or the like and then standing. The solution obtained after such standing is spontaneously separated to the solution phase including the compound represented by the formula (1) or the resin having a structure represented by the formula (2) and the organic solvent, and the aqueous phase, and therefore the solution phase including the compound represented by the formula (1) or the resin having a structure represented by the formula (2) and the organic solvent can be recovered by decantation or the like.

According to the object of the present embodiment, the water used here is preferably water having a low metal content, such as ion-exchange water. The extraction treatment may be performed only once, and is also effectively performed by repeatedly performing operations such as mixing, standing and separation a plurality of times. Conditions such as the proportions of both to be used, the temperature and the time in the extraction treatment are not particularly limited, but may be the same as in the case of the contacting treatment with the acidic aqueous solution.

Water, that can be included in the thus-obtained solution including the compound represented by the formula (1) or the resin having a structure represented by the formula (2) and the organic solvent, can be easily removed by conducting an operation such as evaporation under reduced pressure. The organic solvent can also be if necessary added to adjust the concentration of the compound represented by the formula (1) or the resin having a structure represented by the formula (2) to any concentration.

The method for isolating the compound represented by the formula (1) or the resin having a structure represented by the formula (2) from the resulting solution including the compound represented by the formula (1) or the resin having a structure represented by the formula (2) and the organic solvent is not particularly limited, and can be performed by a known method such as separation by removal under reduced pressure or reprecipitation, and a combination thereof. If necessary, a known treatment such as a concentrating operation, a filtering operation, a centrifugation operation and a drying operation can be performed.

EXAMPLES

Hereinafter, the present embodiment will be more specifically described with reference to Examples. The present embodiment, however, is not limited to these Examples. In the following Synthesis Examples, the structure of a compound was identified by $^1$H-NMR measurement.

Synthesis Example 1

Synthesis of BisN-1

To a container having an inner volume of 100 mL, equipped with a stirrer, a condenser and a burette, were charged 1.60 g (10 mmol) of 2,6-naphthalenediol (reagent produced by Sigma-Aldrich Co., LLC.), 1.82 g (10 mmol) of 4-biphenylaldehyde (produced by Mitsubishi Gas Chemical Company, Inc.) and 30 mL of methyl isobutyl ketone, 5 mL of 95% sulfuric acid was added thereto, and a reaction liquid was stirred at 100° C. for 6 hours to perform a reaction. Then, the reaction liquid was concentrated, 50 g of pure water was added thereto to precipitate a reaction product, and the resultant was cooled to room temperature followed by filtration for separation. A solid obtained by filtration was dried, and separated and purified by column chromatography to thereby provide 3.05 g of an objective compound (BisN-1) represented by the following formula.

Herein, the following peaks were observed by 400 MHz-$^1$H-NMR, and it was confirmed that the compound had a chemical structure of the following formula. In addition, it was confirmed from a doublet signal of protons at 3- and 4-positions that 2,6-dihydroxynaphthol was substituted at 1-position.

$^1$H-NMR: (d-DMSO, Internal reference TMS)
δ (ppm) 9.7 (2H, O—H), 7.2-8.5 (19H, Ph-H), 6.6 (1H, C—H)

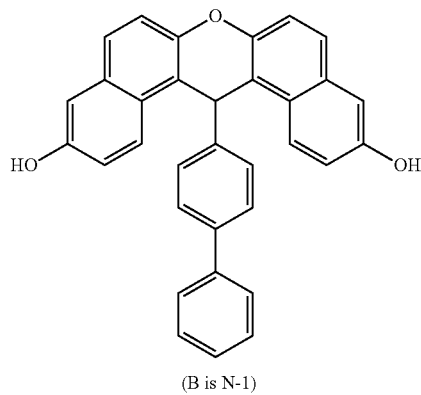 [SMILES: Oc1ccc2c3c(ccc2c1)Oc1ccc2cc(O)ccc2c1C3c1ccc(-c2ccccc2)cc1]

(BisN-1)

Synthesis Example 2

Synthesis of RBisN-1

To a container having an inner volume of 100 mL, equipped with a stirrer, a condenser and a burette, were charged 10 g (21 mmol) of BisN-1, 0.7 g (42 mmol) of paraformaldehyde, 50 mL of glacial acetic acid and 50 mL of PGME, 8 mL of 95% sulfuric acid was added thereto, and a reaction liquid was stirred at 100° C. for 6 hours to perform a reaction. Then, the reaction liquid was concentrated, 1000 mL of methanol was added thereto to precipitate a reaction product, and the resultant was cooled to room temperature followed by filtration for separation. A solid obtained by filtration was dried, and separated and purified by column chromatography to thereby provide 7.2 g of an objective resin (RBisN-1) having a structure represented by the following formula.

The molecular weight in terms of polystyrene with respect to the resulting resin was measured by the above method, and as a result, Mn was 778, Mw was 1793 and Mw/Mn was 2.30.

NMR measurement of the resulting resin was performed under the above measurement conditions, and the following peaks were observed. It was confirmed that the resin had a chemical structure of the following formula.

δ (ppm) 9.7 (2H, O—H), 7.2-8.5 (17H, Ph-H), 6.6 (1H, C—H), 4.1 (2H, —CH$_2$)

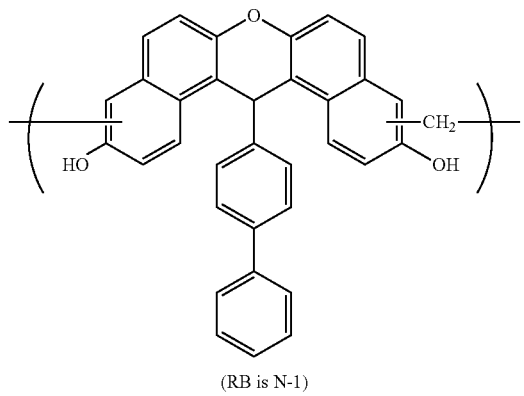

(RB is N-1)

EXAMPLES

Production of propylene glycol monomethyl ether acetate (PGMEA) solution of: compound represented by formula (1) or resin having structure represented by formula (2), either of which has reduced metal content

Example 1

To a four-neck flask (bottom outlet type) having a volume of 1000 mL was charged 150 g of a solution (BisN-1 concentration: 2.5% by weight) including BisN-1 dissolved in PGMEA, and heated to 80° C. with stirring. Next, 37.5 g of an aqueous solution of oxalic acid (pH: 1.3) was added thereto, stirred for 5 minutes, and thereafter left to stand for 30 minutes. Thus, the resultant was spontaneously separated to an oil phase and an aqueous phase, and therefore the aqueous phase was removed. After this operation was repeated once, the resulting oil phase was charged with 37.5 g of ultrapure water, stirred for 5 minutes, and left to stand for 30 minutes to remove the aqueous phase. This operation was repeated three times to thereby provide a solution of BisN-1 having a reduced metal content in PGMEA.

Example 2

Except that 150 g of a solution (BisN-1 concentration: 10% by weight) including PGMEA (120 g)/propylene glycol monomethyl ether (PGME) (15 g) as the solvent was charged instead of 150 g of the PGMEA solution (BisN-1 concentration: 2.5% by weight), the same treatment as in Example 1 was performed to provide a solution of BisN-1 having a reduced metal content in PGMEA/PGME.

Example 3

Except that 130 g of an aqueous solution of citric acid (pH: 1.8) was charged instead of 37.5 g of the aqueous solution of oxalic acid (pH: 1.3), the same treatment as in Example 1 was performed to provide a solution of BisN-1 having a reduced metal content in PGMEA.

Example 4

Except that RBisN-1 was charged instead of BisN-1, the same treatment as in Example 1 was performed to provide a solution (RBisN-1 concentration: 2.5% by weight) of RBisN-1 having a reduced metal content in PGMEA.

Example 5

Except that a solution (BisN-1 concentration: 30% by weight) including methyl isobutyl ketone (150 g) as the solvent was charged instead of 150 g of the PGMEA solution (BisN-1 concentration: 2.5% by weight), the same treatment as in Example 1 was performed to provide a solution of BisN-1 having a reduced metal content in methyl isobutyl ketone.

Example 6

Except that a solution (BisN-1 concentration: 30% by weight) including methyl isobutyl ketone (120 g)/propylene glycol monomethyl ether (PGME) (15 g) as the solvent was charged instead of 150 g of the PGMEA solution (BisN-1 concentration: 2.5% by weight), the same treatment as in Example 1 was performed to provide a solution of BisN-1 having a reduced metal content in methyl isobutyl ketone/PGME.

Example 7

Except that a solution (BisN-1 concentration: 20% by weight) including ethyl acetate (150 g) as the solvent was charged instead of 150 g of the PGMEA solution (BisN-1 concentration: 2.5% by weight), the same treatment as in Example 1 was performed to provide a solution of BisN-1 having a reduced metal content in ethyl acetate.

Example 8

Except that a solution (BisN-1 concentration: 20% by weight) including ethyl acetate (120 g)/propylene glycol monomethyl ether (PGME) (15 g) as the solvent was charged instead of 150 g of the PGMEA solution (BisN-1 concentration: 2.5% by weight), the same treatment as in Example 1 was performed to provide a solution of BisN-1 having a reduced metal content in ethyl acetate/PGME.

Example 9

Except that RBisN-1 was charged instead of BisN-1, the same treatment as in Example 6 was performed to provide a solution (RBisN-1 concentration: 30% by weight) of RBisN-1 having a reduced metal content in methyl isobutyl ketone/PGME.

Example 10

Except that RBisN-1 was charged instead of BisN-1, the same treatment as in Example 8 was performed to provide a solution (RBisN-1 concentration: 20% by weight) of RBisN-1 having a reduced metal content in ethyl acetate/PGME.

Reference Example 1

Except that 150 g of a PGMEA solution (BisN-1 concentration: 10% by weight) was charged instead of 150 g of the PGMEA solution (BisN-1 concentration: 2.5% by weight), the same operation as in Example 1 was started. An aqueous solution of oxalic acid (pH: 1.3) (37.5 g) was added and stirred for 5 minutes to precipitate a part of BisN-1. Then, the resultant was heated to 80° C. and thereafter further stirred for 5 minutes to provide a solution (BisN-1 concentration: 10% by weight) of BisN-1 having a reduced metal content in PGMEA.

Comparative Example

Production of Cyclic Compound, having Reduced Metal Content, by Ion-Exchange Resin Comparative Example 1

Twenty five g of an ion-exchange resin (DIAION produced by Mitsubishi Chemical Corporation: SMT100-Mixed resin) was swollen by cyclohexanone and thereafter filled in a Teflon (registered trademark) column, and 500 mL of 1,3-dioxolane was allowed to pass therethrough to thereby perform solvent replacement. Then, 500 g of a solution (1.7% by weight) including BisN-1 dissolved in 1,3-dioxolane was allowed to pass therethrough to provide a solution of BisN-1 in dioxane.

Various metal contents were measured by ICP-MS with respect to a 10% by weight BisN-1 solution in PGMEA before treatment, a 10% by weight RBisN-1 solution in PGMEA before treatment, and the solution of the compound represented by the formula (1) or formula (2) obtained in each of Examples 1 to 10 and Comparative Example 1. The measurement results are shown in Table 1.

TABLE 1

| | Metal content (ppb) | | | | | |
|---|---|---|---|---|---|---|
| | Na | Mg | K | Fe | Cu | Zn |
| BisN-1 (before treatment) | 35 | 1.2 | 1.2 | >99 | 2.7 | 13.6 |
| RBisN-1 (before treatment) | 46 | 2.2 | 13 | >99 | 3.5 | 7.4 |
| Example 1 | ≤0.2 | ≤0.2 | ≤0.2 | ≤0.2 | ≤0.2 | ≤0.2 |
| Example 2 | ≤0.2 | ≤0.2 | ≤0.2 | ≤0.2 | ≤0.2 | ≤0.2 |
| Example 3 | ≤0.2 | ≤0.2 | ≤0.2 | ≤0.2 | ≤0.2 | ≤0.2 |
| Example 4 | ≤0.2 | ≤0.2 | ≤0.2 | ≤0.2 | ≤0.2 | ≤0.2 |
| Example 5 | ≤0.2 | ≤0.2 | ≤0.2 | ≤0.2 | ≤0.2 | ≤0.2 |
| Example 6 | ≤0.2 | ≤0.2 | ≤0.2 | ≤0.2 | ≤0.2 | ≤0.2 |
| Example 7 | ≤0.2 | ≤0.2 | ≤0.2 | ≤0.2 | ≤0.2 | ≤0.2 |
| Example 8 | ≤0.2 | ≤0.2 | ≤0.2 | ≤0.2 | ≤0.2 | ≤0.2 |
| Example 9 | ≤0.2 | ≤0.2 | ≤0.2 | ≤0.2 | ≤0.2 | ≤0.2 |
| Example 10 | ≤0.2 | ≤0.2 | ≤0.2 | ≤0.2 | ≤0.2 | ≤0.2 |
| Comparative Example 1 | ≤0.2 | 0.5 | 1.0 | >99 | 1.2 | 0.4 |

The present application is based on Japanese Patent Application (Japanese Patent Application No. 2013-248012) filed on Nov. 29, 2013, and the content thereof is herein incorporated by reference.

According to the present invention, the compound represented by the formula (1) or the resin having a structure represented by the formula (2), either of which has a reduced metal content, can be industrially advantageously produced.

The invention claimed is:

1. A method for purifying a compound represented by the following formula (1) or a resin having a structure represented by the following formula (2), the method comprising:
a step of bringing a solution (A) comprising an organic solvent optionally immiscible with water, and the compound or the resin into contact with an acidic aqueous solution;

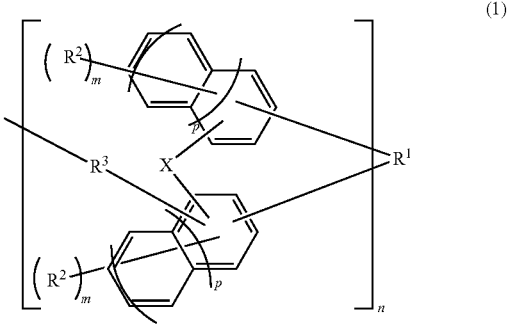

(1)

wherein, each X independently represents an oxygen atom or a sulfur atom, $R^1$ represents a single bond or a 2n-valent hydrocarbon group having 1 to 30 carbon atoms, the hydrocarbon group optionally has a cyclic hydrocarbon group, a double bond, a hetero atom, or an aromatic group having 6 to 30 carbon atoms, and each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group, each m is independently an integer of 1 to 6, each p is independently 0 or 1, and n is an integer of 1 to 4;

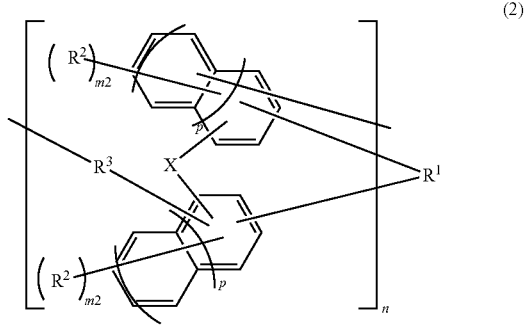

(2)

wherein, each X independently represents an oxygen atom or a sulfur atom, $R^1$ represents a single bond or a 2n-valent hydrocarbon group having 1 to 30 carbon atoms, the hydrocarbon group optionally has a cyclic hydrocarbon group, a double bond, a hetero atom, or an aromatic group having 6 to 30 carbon atoms, each $R^2$ independently represents a linear, branched or cyclic alkyl group having 1 to 10 carbon atoms, an aryl group having 6 to 10 carbon atoms, an alkenyl group having 2 to 10 carbon atoms, or a hydroxyl group, provided that at least one $R^2$ represents a hydroxyl group, each $R^3$ independently represents a single bond, or a linear or branched alkylene group having 1 to 20 carbon atoms, each $m^2$ is independently an integer of 1 to 5, each p is independently 0 or 1, and n is an integer of 1 to 4.

2. The method according to claim 1, wherein the acidic aqueous solution is one or more aqueous solution of mineral acid selected from the group consisting of hydrochloric acid, sulfuric acid, nitric acid and phosphoric acid, or one or more aqueous solution of organic acid selected from the group consisting of acetic acid, propionic acid, oxalic acid, malonic acid, succinic acid, fumaric acid, maleic acid, tartaric acid, citric acid, methanesulfonic acid, phenolsulfonic acid, p-toluenesulfonic acid and trifluoroacetic acid.

3. The method according to claim 1, wherein the organic solvent optionally immiscible with water is toluene, 2-heptanone, cyclohexanone, cyclopentanone, methyl isobutyl ketone, propylene glycol monomethyl ether acetate or ethyl acetate.

4. The method according to claim 1, wherein the organic solvent optionally immiscible with water is methyl isobutyl ketone or ethyl acetate.

5. The method according to claim 1, wherein the solution (A) comprises the organic solvent optionally miscible with water in an amount of 0.1 to 100 times by mass based on an amount of the compound represented by the formula (1) or the resin having the structure represented by the formula (2).

6. The method according to claim 5, wherein the organic solvent optionally miscible with water is N-methylpyrrolidone or propylene glycol monomethyl ether.

7. The method according to claim 1, further comprising a step of performing an extraction treatment with water after an extraction treatment by the step of bringing the solution (A) into contact with the acidic aqueous solution is performed.

8. The method according to claim 1, wherein the compound represented by the formula (1) is a compound represented by the following formula (1-1):

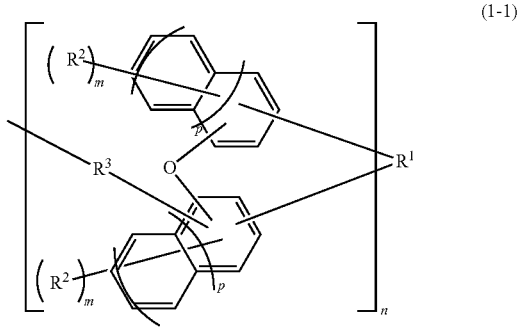

(1-1)

wherein, $R^1$, $R^2$, m, p and n are the same as defined in the formula (1).

9. The method according to claim 8, wherein the compound represented by the formula (1-1) is a compound represented by the following formula (1-2):

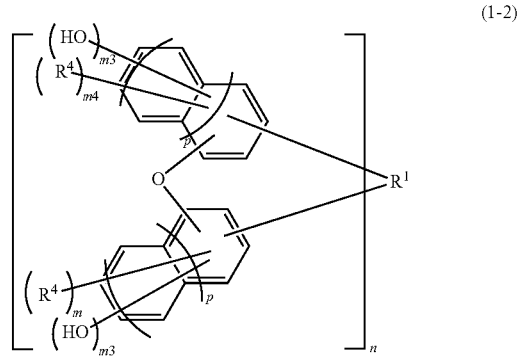

(1-2)

wherein, $R^1$, p and n are the same as defined in the formula (1), $R^4$ is the same as $R^2$ defined in the formula (1), each $m^3$ is independently an integer of 1 to 6, each $m^4$ is independently an integer of 0 to 5, and $m^3 + m^4$ is an integer of 1 to 6.

10. The method according to claim 9, wherein the compound represented by the formula (1-2) is compound represented by the following formula (1-3)

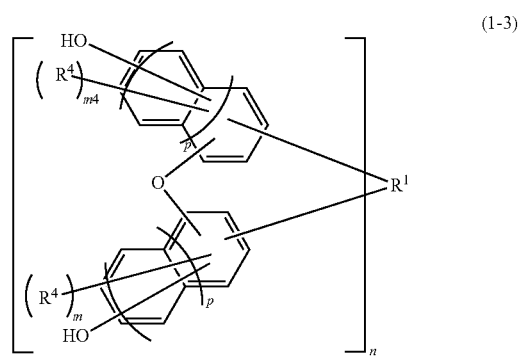

(1-3)

wherein, $R^1$, p and n are the same as defined in the formula (1), and $R^4$ and $m^4$ are the same as defined in the formula (1-2).

11. The method according to claim 1, wherein the compound represented by the formula (1) is a compound represented by the following formula (1-4):

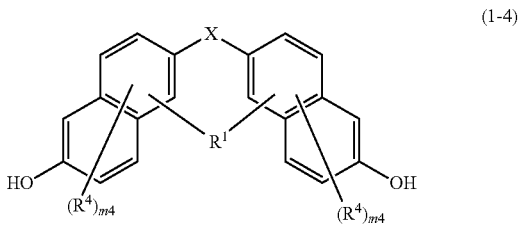

(1-4)

wherein, X and $R^1$ are the same as defined in the formula (1), $R^4$ is the same as $R^2$ defined in the formula (1), and each $m^4$ is independently an integer of 0 to 5.

12. The method according to claim 11, wherein the compound represented by the formula (1-4) is a compound represented by the following formula (1-5):

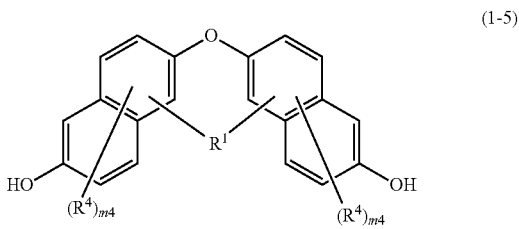

(1-5)

wherein, $R^1$ is the same as defined in the formula (1), $R^4$ is the same as $R^2$ defined in the formula (1), and each $m^4$ is independently an integer of 0 to 5.

13. The method according to claim 12, wherein the compound represented by the formula (1-5) is a compound represented by the following formula (BisN-1):

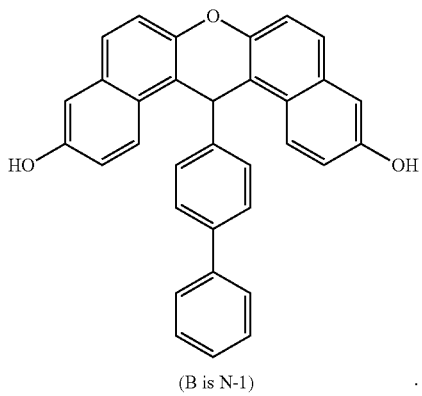 [SMILES: Oc1ccc2c3c(ccc2c1)Oc1ccc2cc(O)ccc2c1C3c1ccc(-c2ccccc2)cc1]
(B is N-1)
* * * * *